(12) United States Patent
Elsharif

(10) Patent No.: US 12,091,321 B2
(45) Date of Patent: Sep. 17, 2024

(54) SOLID NANOMATERIAL ADSORBENT

(71) Applicant: Imam Abdulrahman Bin Faisal University, Dammam (SA)

(72) Inventor: Asma Mohammed Elsharif, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 18/624,173

(22) Filed: Apr. 2, 2024

(65) Prior Publication Data

US 2024/0246824 A1    Jul. 25, 2024

Related U.S. Application Data

(63) Continuation of application No. 17/681,195, filed on Feb. 25, 2022, now Pat. No. 11,987,500.

(51) Int. Cl.
*C01B 32/168* (2017.01)
*B82Y 30/00* (2011.01)
(Continued)

(52) U.S. Cl.
CPC .......... *C01B 32/168* (2017.08); *C07D 487/22* (2013.01); *B82Y 30/00* (2013.01); *B82Y 40/00* (2013.01); *C01P 2004/13* (2013.01)

(58) Field of Classification Search
CPC ... C01B 32/168; C01B 32/174; C01B 32/158; C01B 32/159; C01B 32/16;
(Continued)

(56) References Cited

U.S. PATENT DOCUMENTS 11,987,500 B2 * 5/2024 Elsharif ................ C01B 32/174

FOREIGN PATENT DOCUMENTS

| CN | 105129898 B | 12/2017 |
|---|---|---|
| CN | 110252257 A | 9/2019 |
| CN | 112316927 A | 2/2021 |

OTHER PUBLICATIONS

Qu, et al., Amine-linker length dependent electron transfer between porphyrins and covalent amino-modified single-walled carbon nanotubes, RSC Advances 2011; 1: 632-639 (Year: 2011).*

(Continued)

*Primary Examiner* — Daniel C. McCracken
(74) *Attorney, Agent, or Firm* — Oblon, McClelland, Maier & Neustadt, L.L.P.

(57) ABSTRACT

A nanomaterial and a method of preparing the nanomaterial are provided. The nanomaterial is a product formed by a reaction of functionalized carbon nanotube comprising first and second aminoalkyl groups covalently bonded to a surface of the carbon nanotube and a porphyrin ring of formula (I). A method of removing a pollutant from an aqueous solution by contacting the aqueous solution having an initial concentration of the pollutant with the nanomaterial is also provided.

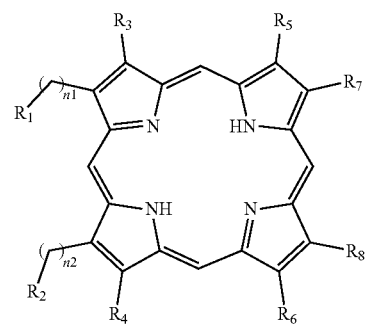

17 Claims, 7 Drawing Sheets

(51) Int. Cl.
*B82Y 40/00* (2011.01)
*C07D 487/22* (2006.01)

(58) Field of Classification Search
CPC ... C01B 32/162; C01B 32/164; C01B 32/166; C01B 32/17; C01B 32/172; C01B 32/176; C01B 32/178; C01B 2202/00; C01B 2202/02; C01B 2202/04; C01B 2202/06; C01B 2202/08; C01B 2202/10; C01B 2202/20; C01B 2202/22; C01B 2202/24; C01B 2202/26; C01B 2202/28; C01B 2202/30; C01B 2202/32; C01B 2202/34; C01B 2202/36; C07D 487/22; B82Y 30/00; B82Y 40/00; C01P 2004/13; D01F 9/12; D01F 9/127; D01F 9/1271; D01F 9/1272; D01F 9/1273; D01F 9/1274; D01F 9/1275; D01F 9/1276; D01F 9/1277; D01F 9/1278; D01F 9/133
See application file for complete search history.

(56) References Cited

OTHER PUBLICATIONS

Banerjee, et al., Photoactivated Antimicrobial Activity of Carbon Nanotube-Porphyrin Conjugates, Langmuir 2010; 26(22): 17369-17374 (Year: 2010).*

Saeed Rayati, et al., "Manganese(III) porphyrin supported onto multi-walled carbon nanotubes for heterogeneous oxidation of synthetic textile dyes and 2,6-dimethylphenol by tert-butyl hydroperoxide", Comptes Rendus Chimie, vol. 19, No. 3, 2016, pp. 371-380.

G Prabhavathi, et al., "Synthesis, characterization and photoluminescence properties of tetra(aminophenyl) porphyrin covalently linked to multi-walled carbon nanotubes", Journal of Chemical Sciences, vol. 129, No. 6, Jun. 2017, pp. 699-706.

Konggang Qu, et al., "Amine-linker length dependent electron transfer between porphyrins and covalent amino-modified single-walled carbon nanotubes", RSC Advances, Royal Society of Chemistry, vol. 1, Issue 4, Aug. 23, 2011, 17 pages.

* cited by examiner

SOLID NANOMATERIAL ADSORBENT

CROSS-REFERENCE TO RELATED APPLICATIONS

The present application is a Continuation of U.S. application Ser. No. 17/681,195, now allowed, having a filing date of Feb. 25, 2022.

BACKGROUND

Technical Field

The present disclosure relates to a nanomaterial, method of preparation and application thereof. More specifically, the present disclosure relates to a method of removing a pollutant from an aqueous solution using the nanomaterial.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Water is regarded as a vitally essential element for earth life. However, drinking water sources are contaminated through industrial effluents, oil spillages, radioactive isotopes, and agricultural runoff [Palansooriya, K. N. et al. Crit. Rev. Environ. Sci. Technol. 50, 549-611, 2020]. Pollution of water due to organic dyes has severely influenced health due to toxic effects. Industrial dyes are mainly classified into acid dyes, basic dyes, direct dyes, disperse dyes, reactive dyes, fluorescent brighteners, mordant, sulfur dyes, vat dyes, and solvent dyes [Hunger, Klaus Industrial Dyes: Chemistry, Properties, Applications 3-5, 2007]. Industrial dyes have caused widespread concern for their contribution to pollution of water bodies. Such chemical pollutants may be metabolized and decomposed into aromatic amines after entering the human body, and have high toxicity, high residue, "three causes" (carcinogenic, teratogenic, mutagenic) and other toxic side effects. Therefore, in recent years, research on the control of industrial dyes and organic pollutants in water bodies has become a hot spot in the field of water treatment.

Methylene blue is a kind of phenothiazine salt which is widely used in chemical indicators, dyes, biological stains. Methylene blue also has a good effect on prevention and treatment of water mold and small melon worm disease in freshwater fish and may be used in aquaculture. Methylene blue brings skin-related issues at a lower dose (2-4 mg/kg) [Jack, I. I. et al. Am. J. Ther. 10, 289-291, 2003]. In addition, the mixing of organic dyes in water may change its quality and cause death of living organisms [Lellis, B. et al. Biotechnol. Res. Innov. 3, 275-290, 2019]. Organic dyes are commonly used in many industries like paper, plastic, textile, pharmaceutical, cosmetic, and food [Raina, S. et al. Environ. Nanotechnology, Monit. Manag. 13, 100278, 2020]. Most often used organic dyes in the industrial process include methylene blue, methyl orange, methyl red, congo red, phenol red, eosin Y, bromophenol blue, acridine orange, etc. [Khan, H. et al. J. Chem. Eng. 33, 2802-2807, 2016; Roy, A. et al. Bioinspired, Biomim. Nanobiomaterials. 8, 130-140, 2019]. It is important to completely eradicate dyes prior to discharging industrial waste to minimize their impact on water pollution, as dyes are generally stable in water due to their biologically non-degradable structure [Raina, S. et al. Environ. Nanotechnology, Monit. Manag. 13, 100278, 2020].

Different technologies have emerged for dye elimination from contaminated water which include photocatalytic degradation, electrochemical degradation, membrane filtration, ultrafiltration, nanofiltration, ozonation, biological treatment, ion-exchange, chemical precipitation chemical oxidation, solvent extraction, and coagulation/flocculation [Rasheed, T. et al. Environ. Int. 122, 52-66, 2019]. Among the existing technologies, adsorption is the most promising method for effective elimination of dyes from wastewater due to its wide applicability, low cost, ease of operation, and low energy consumption [Al-Hammadi, S. A. et al. J. Environ. Manage. 226, 358-364, 2018]. Removal of dyes from water has been investigated using several sorbents, e.g. activated carbon, graphene oxide, nanomaterials, smart materials, nanocomposites, etc. [Pathania, D. et al. Arab. J. Chem. 10, S1445-S1451, 2017; Novais, R. M. et al. J. Clean. Prod. 207, 350-362, 2019; Mouni, L. et al. Appl. Clay Sci. 153, 38-45, 2018; Wang, N. et al. Powder Technol. 347, 93-102, 2019; Huang, T. et al. J. Colloid Interface Sci. 543, 43-51, 2019].

The emergence of nanomaterials represents an active area and opens daylight for research in various application fields. Over the last two decades, carbon nanotubes have been broadly applied in the field of adsorption and have been considered by many researchers as a lead for removal of contaminants from polluted water due to their excellent mechanical properties, thermal properties, electrical properties, large specific surface area, high transparency, large surface-to-volume ratio, and chemical stability [Gupta, V. K. et al. Adv. Colloid Interface Sci. 193, 24-34, 2013; Rahimi, K. et al. J. Environ. Manage. 242, 81-89, 2019].

CN105129898B disclosed a renewable amino functionalized magnetic carbon nano composite material for removing acidic dyes from water and preparation method thereof. The composite material was prepared from carbon nanotubes and amino functional agent as raw materials, wherein the amino functional agent includes ethylenediamine. However, a porphyrin linked amine functionalized carbon nanotube was not disclosed. Also, a method for removal of methylene blue (basic dye) and heavy metals from wastewater using the nanocomposite material is not disclosed.

CN112316927A disclosed a modified carbon nanotube/polyacrylonitrile composite material for rapidly adsorbing methylene blue and a preparation method thereof. The composite material was prepared from carbon nanotube, acrylonitrile and polymerizable glycidyl ether as raw materials. The composite material was used as a rapid adsorbent for the adsorption of methylene blue, so that the adsorption amount of methyl blue is large, and the adsorption time is short. However, a porphyrin linked amine functionalized carbon nanotube was not disclosed. Also, a method for removal of heavy metals using the composite material is not disclosed.

Qu et al. [RSC advances, 1, 632-639, 2011] disclosed a covalent amine-modified single-walled carbon nanotube with different alkyl chain lengths. However, a porphyrin linked amino-functionalized carbon nanotube was not disclosed. Also, a method for removal of organic dye and heavy metals from wastewater using the amine-modified single carbon nanotube is not disclosed.

Porphyrins and their derivatives are significant functional molecules and a category of organic chromophores [Shi, Y. et al. Dye Pigm. 188, 109136, 2021]. Porphin is the simplest unsubstituted porphyrin. The porphyrin macrocycle possesses 26 electrons, among these, 18 are delocalized π electrons leading to planar macrocycle [Soury, R. et al. Chem. Eng. J. 375, 122005, 2019]. The molecules of porphyrins have four pyrrole units connected by methine bridges possessing a square planar structure [Hiroto, S. et al. Chem. Rev. 117, 2910-3043, 2017; Tanaka, T. et al. Chem. Soc. Rev. 44, 943-969, 2015; Marbach, H. Acc. Chem. Res. 48, 2649-2658, 2015]. Several functional groups are introduced on porphin macrocycles at the meso-position and the β-position creating many efficient porphyrin derivatives [Gottfried, J. M. Surf. Sci. Rep. 70, 259-379, 2015]. Moreover, free-base porphyrins are coordinated with various metal ions at the center of porphyrin to produce metal complexes, called metalloporphyrins [Adler, A. D. et al. J. Inorg. Nucl. Chem. 32, 2443-2445, 1970]. Also, porphyrins and porphyrin derivatives have attracted a lot of attention as materials that display great potential for catalysis [Kobayashi, N. et al. Inorg. Chem. 31, 5172-5177, 1992], biosensors [Lanzilotto, A. et al. J. Biol. Inorg. Chem. 23, 109-122, 2018; Singh, S. Chem. Rev. 115, 10261-10306, 2015], nonlinear optical devices, solar cells [Weinkauf, J. R. et al. J. Phys. Chem. A. 107, 3486-3496, 2003; Lind, S. J. et al. Phys. Chem. Chem. Phys. 11, 5598-5607, 2009; Lu, Y. et al. ChemSusChem. 12, 2802-2809, 2019; Zeng, K. et al. J. Am. Chem. Soc. 142, 5154-5161, 2020; Martinez-Diaz, M. V. et al. Chem. Commun. 46, 7090-7108, 2020] emitting diodes [Drouet, S. et al. New J. Chem. 35, 438-444, 2011] and recently for gas adsorption [Soury, R. et al. Chem. Eng. J. 375, 122005, 2019]. Such a great concern in these molecules is essentially owing to their chemical structure, as well as the biological and electrical properties.

CN110252257A disclosed a carbon nanotube metal organic framework (MOFS) composite material for adsorption of anionic organic dyes in a water phase, a preparation method and application thereof. The carbon nanotube MOFS composite material has high specific surface area and shows superior selective adsorption performance on anionic dyes in wastewater in an aqueous solution. The carbon nanotube MOFS composite material was prepared from surface carboxyl functionalized carbon nanotubes, a metal precursor and an organic ligand as raw materials, wherein the organic ligand includes mes-tetrakis(4-carboxyphenyl) porphin. However, a method for removal of methylene blue (basic dye) and heavy metals from wastewater using the carbon nanotube MOFS is not disclosed.

A nanocatalyst i.e. manganese porphyrin supported onto multi-walled carbon nanotubes was disclosed by Saeed et al. [Comptes Rendus Chimie 19, 371-380, 2016] for oxidative degradation of synthetic textile dyes, wherein the textile dyes includes methylene blue. Ten percent of methylene blue was adsorbed onto the surface of the supported catalyst and 90% was degraded during oxidative degradation experiment. However, a method for removal of heavy metals from wastewater using the nanocatalyst is not disclosed.

Prabhavathi et al. [J. Chem. Sci. 129, 699-706, 2017] disclosed a nano hybrid of 5,10,15,20-mesotetra(4-aminophenyl) porphyrin functionalized with multi-walled carbon nanotubes through an amide linkage. However, a method for removal of organic dye and heavy metals from wastewater using the nano hybrid is not disclosed.

Despite these recent advances in nanomaterials, the drawbacks of each of the aforementioned nanomaterials and/or methods indicate that there is still a need for development of nanomaterials for removal of organic dyes and heavy metals from wastewater.

SUMMARY

In an exemplary embodiment, a nanomaterial is disclosed. The nanomaterial is a product formed by a reaction of a functionalized carbon nanotube comprising first and second aminoalkyl groups covalently bonded to a surface of the carbon nanotube and a porphyrin ring of formula (I)

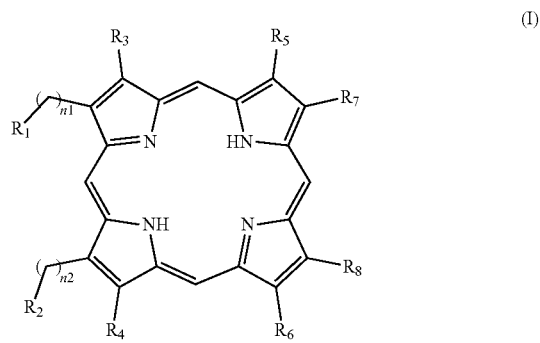

or a salt thereof, a solvate thereof, a tautomer thereof, a stereoisomer thereof, a metalation product thereof, or a mixture thereof. The first and second aminoalkyl groups are each independently a $C_{1-6}$ alkyl substituted with at least one primary or secondary amino group; $R_1$ and $R_2$ are independently —COOH or an activated carbonyl group; $R_3$, $R_4$, $R_5$, $R_6$, $R_7$, and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl; $n_1$ and $n_2$ are independently an integer in a range of 1-6. The functionalized carbon nanotube is bonded with the porphyrin ring of formula (I) via two amide linkages, one formed between $R_1$ of the porphyrin ring and the first aminoalkyl group of the functionalized carbon nanotube, and the other between $R_2$ of the porphyrin ring and the second aminoalkyl group of the functionalized carbon nanotube.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein the functionalized carbon nanotube is a multi-walled carbon nanotube.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein the first and second aminoalkyl groups are —CH$_2$CH$_2$NH$_2$.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_1$ and $R_2$ are —COOH.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $n_1$ and $n_2$ are 1.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_3$ and $R_4$ are —$CH_3$.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_5$ and $R_8$ are independently —$CH_3$ or —$CH=CH_2$.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_6$ and $R_7$ are independently —$CH_3$ or —$CH(OH)CH_3$.

In some embodiments, the nanomaterial is a product formed by the reaction of the functionalized carbon nanotube comprising first and second aminoalkyl groups covalently bonded to a surface of the carbon nanotube and the porphyrin ring of formula (I), wherein the porphyrin ring is

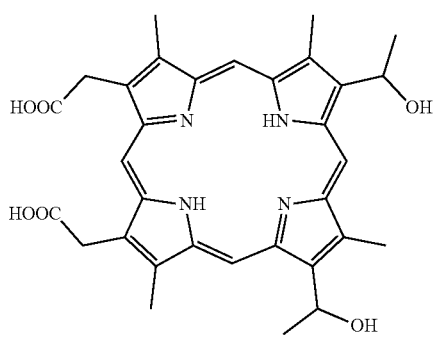 [SMILES: CC1=C(CC(=O)O)c2cc3[nH]c(cc4nc(cc5[nH]c(cc1n2)c(C)c5C(C)O)C(C)=C4C(C)O)c(C)c3CC(=O)O]

In some embodiments, the nanomaterial is a product formed by the reaction of the functionalized carbon nanotube comprising first and second aminoalkyl groups covalently bonded to a surface of the carbon nanotube and metalation product of porphyrin ring of formula (I), wherein the metalation product of porphyrin ring of formula (I) is of formula (II)

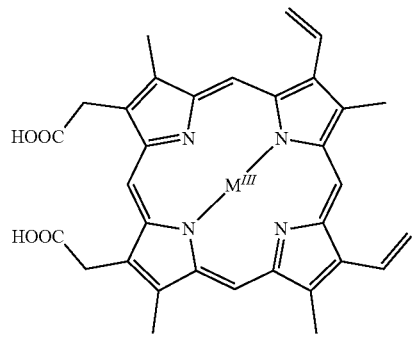

wherein M is a metal selected from the group consisting of Mn, Fe, and Co.

In some embodiments, the nanomaterial is a product formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein a shortest distance between the first and second aminoalkyl groups on the surface of the functionalized carbon nanotube is about 0.1-10 nm.

In another exemplary embodiment, a method of preparing the nanomaterial is described. The method comprises mixing the functionalized carbon nanotube with the porphyrin ring of formula (I) thereby forming the nanomaterial.

In some embodiments, the method comprises mixing the functionalized carbon nanotube with the porphyrin ring of formula (I) thereby forming the nanomaterial, wherein $R_1$ and $R_2$ are —COOH, and wherein the mixing occurs in the presence of an amide bond formation coupling reagent.

In some embodiments, the method comprises mixing the functionalized carbon nanotube with the porphyrin ring of formula (I) thereby forming the nanomaterial, wherein the first and second aminoalkyl groups are —$CH_2CH_2NH_2$, and the amine functionalized carbon nanotube is prepared by mixing a carbon nanotube with ethylene diamine in the presence of a nitrite salt and a strong acid.

In yet another exemplary embodiment, a method for removing a pollutant from an aqueous solution is described. The method comprises contacting the aqueous solution having an initial concentration of the pollutant with the nanomaterial to form a mixture and filtering the mixture to obtain an aqueous solution having a reduced concentration of the pollutant compared to the initial concentration. The initial concentration of the pollutant in the aqueous solution is in a range of 10 to 1000 mg $L^{-1}$ and the nanomaterial is present in a concentration ranging from about 0.001 to 10 g per liter of the aqueous solution during the contacting. The nanomaterial is contacted with the aqueous solution at a temperature in a range of about 10° ° C. to 80° ° C. for 0.1 to 24 hours.

In some embodiments, the method for removing a pollutant from aqueous solution comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is an organic dye, a heavy metal, or both.

In some embodiments, the method for removing a pollutant from aqueous solution comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is an organic dye and wherein the organic dye is methylene blue.

In some embodiments, the method for removing a pollutant from aqueous solution comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is a heavy metal, and wherein the heavy metal is an ion of at least one heavy metal selected from the group consisting of Ni, Cd, Pb, As, Cr, Cu, and Fe.

In some embodiments, the method for removing a pollutant from aqueous solution comprises contacting the aqueous solution having an initial concentration of the pollutant with the nanomaterial to form a mixture and filtering the mixture to obtain an aqueous solution having a reduced concentration of the pollutant compared to the initial concentration, wherein the aqueous solution has a pH in a range of about 3 to 7.

In some embodiments, the method for removing a pollutant from aqueous solution comprises contacting the aqueous solution having an initial concentration of the pollutant with the nanomaterial to form a mixture and filtering the mixture to obtain an aqueous solution having a reduced concentration of the pollutant compared to the initial concentration, wherein greater than about 75% of a total mass of the pollutant is removed from the aqueous solution.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
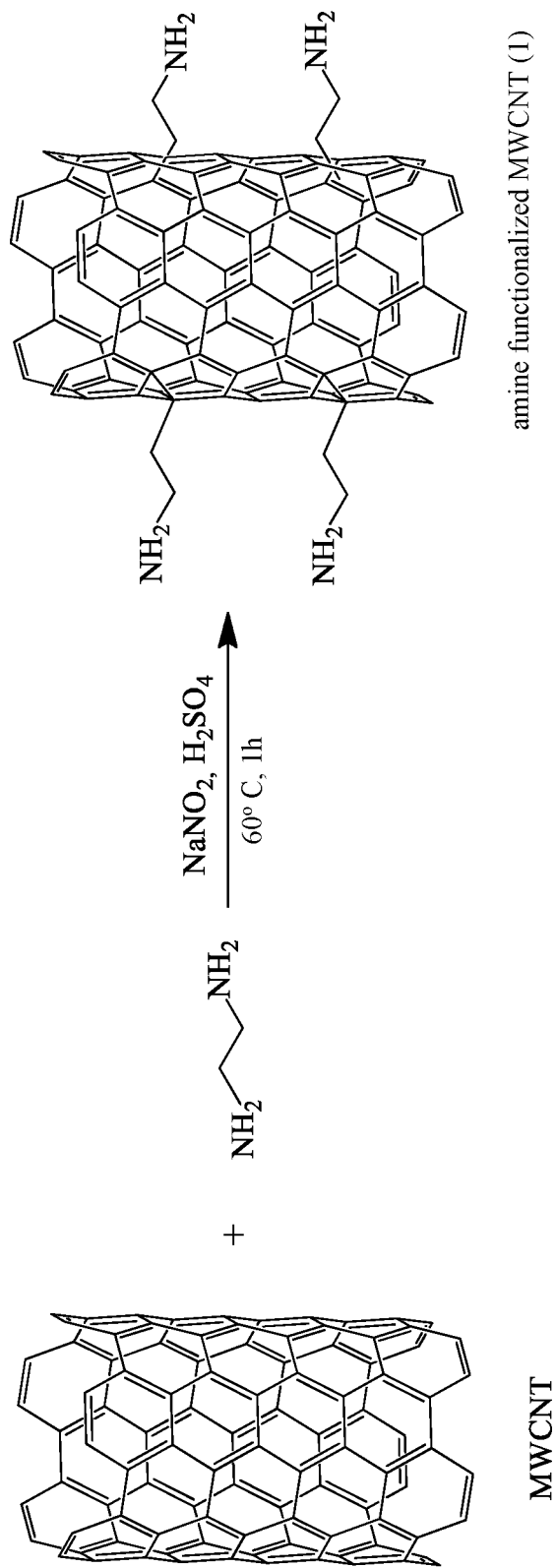
FIG. 1 is a scheme for synthesis of amine functionalized carbon nanotube (1).

When describing the present disclosure, the terms used are to be construed in accordance with the following definitions, unless a context dictates otherwise.

Embodiments of the present invention will now be described more fully hereinafter with reference to the accompanying drawings, in which some, but not all embodiments of the disclosure are shown.

In the drawings, like reference numerals designate identical or corresponding parts throughout the several views. Further, as used herein, the words "a," "an" and the like generally carry a meaning of "one or more" unless stated otherwise.

Furthermore, the terms "approximately", "approximate", "about," and similar terms generally refer to ranges that include the identified value within a margin of 20%, 10%, or preferably 5%, and any values therebetween.

The term "substantially ionic" as used herein, refers to a bond having about 80% ionic character, preferably more than about 90% ionic character, even more preferably more than about 95% ionic character, and most preferably more than about 97% ionic character.

The term "porphyrin ring of formula (I)" as used herein, refers to include a salt thereof, a solvate thereof, a tautomer thereof, a stereoisomer thereof, a metalation product thereof, or a mixture thereof.

The term "porphyrin ring of formula (II)" as used herein, refers to include a salt thereof, a solvate thereof, a tautomer thereof, a stereoisomer thereof, a metalation product thereof, or a mixture thereof.

The term "salt" as used herein, refers to an ionic compound that does or may result from a neutralization reaction between an acid and a base.

The term "solvate" as used herein, refers to hydrates and solvent addition forms which the porphyrin ring of formula (I) or the porphyrin ring of formula (II) is able to form, as well as salts thereof. Examples of such forms are e.g. hydrates, alcoholates and the like.

The term "tautomer" as used herein, refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

The terms "stereoisomers", "stereoisomeric forms" or "stereochemically isomeric forms" as used herein, are used interchangeably.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. not related as mirror images. If a compound contains a double bond, the substituents may be in the E or the Z configuration. Substituents on bivalent cyclic (partially) saturated radicals may have either the cis- or trans-configuration; for example, if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to those skilled in the art.

It follows that porphyrin ring of formula (I) may exist in both stereoisomeric and tautomeric form.

The term "metalation" as used herein, refers to formation of a nitrogen-metal bond, and characteristics of the bond may be substantially ionic.

In the framework of this disclosure, an element, in particular when mentioned in relation to the porphyrin ring of formula (I) or the porphyrin ring of formula (II), comprises all isotopes and isotopic mixtures of this element, either naturally occurring or synthetically produced, either with natural abundance or in an isotopically enriched form. Radiolabelled compounds of the porphyrin ring of formula (I) or the porphyrin ring of formula (II) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H.

In particular, deuterated compounds are intended to be included within the scope of the present disclosure.

The term "aminoalkyl" as used herein, refers to a linear or branched chain alkyl group substituted with one or more amino groups. Some non-limiting examples of the aminoalkyl group include aminomethyl, aminoethyl, aminopropyl, aminobutyl and aminohexyl. The aminoalkyl group is optionally substituted with one or more substituents described herein.

The term "substituted" as used herein, unless otherwise indicated or is clear from the context, refers to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture.

The term "optionally substituted" as used herein, refers to a radical or a group that is unsubstituted or is substituted.

The term "alkyl" as used herein, and unless otherwise specified, refers to both linear and branched chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "alkenyl" as used herein, refers to a saturated linear or branched chain, cyclic or non-cyclic hydrocarbon, or combination thereof having from 1 to 21 carbon atoms and having at least one carbon-carbon double bond. Representative linear and branched chain alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

The term "aryl" as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "cycloalkyl" as used herein, refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "heteroaryl" as used herein, and unless otherwise specified, refers to aryl group containing one or more heteroatoms. Non-limiting examples of heteroatoms include O, N, and S.

The term "heterocyclic" as used herein refers to a saturated, partially saturated, or fully unsaturated cyclic hydrocarbon group having one or more heteroatoms which may be unsubstituted or substituted by one or more of the substituents as indicated herein.

The term "halogen" as a group or part of a group is generic for fluoro, chloro, bromo, iodo unless otherwise is indicated or is clear from the context.

The term "alkoxy" as used herein, refers to a group wherein the alkyl group is attached to an oxygen atom, and the "alkyl" part is the same as defined in the above-mentioned "alkyl".

The term "heteroaryloxy" as used herein, refers to a substituted hydroxyl of formula (—OR$^a$), wherein Ra is an optionally substituted heteroaryl group, as defined herein, and the oxygen moiety is directly attached to parent molecule.

The term "heterocyclyloxy" as used herein, refers to a substituted hydroxyl of formula (—OR$^b$), wherein Rb is an optionally substituted heterocyclic group, as defined herein, and the oxygen moiety is directly attached to parent molecule.

The prefix "C$_{x-y}$" (where x and y are integers) as used herein, refers to the number of carbon atoms in a given group. Thus, a C$_{1-6}$ alkyl group contains from 1 to 6 carbon atoms, a C$_{1-8}$ alkyl group contains from 1 to 8 carbon atoms, and so on.

The term "C$_{1-6}$ alkyl" as used herein, refers to a hydrocarbyl radical of formula C$_n$H$_{2n+1}$ wherein n is a number ranging from 1 to 6. C$_{1-6}$ alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched chain and may be substituted as indicated herein. C$_{1-6}$ alkyl includes all linear or branched chain alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "C$_{1-6}$ alkenyl" as used herein, refers to an alkenyl radical having from 1 to 6 carbon atoms. Non-limiting examples of suitable C$_{1-6}$ alkenyl include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, and 3-hexenyl.

The term "C$_{1-6}$ cycloalkyl" alone or in combination, refers to a cyclic saturated hydrocarbon radical having from 1 to 6 carbon atoms. Non-limiting examples of suitable C$_{1-6}$ cycloalkyl include cyclopropyl, cyclobutyl, cyclopentyl, and cyclohexyl.

The term "activated carbonyl" as used herein, refers to a functional group having a formula of —C(O)R$^e$, wherein Re is a halogen, optionally substituted alkoxy, optionally substituted aryloxy, optionally substituted heteroaryloxy, optionally substituted heterocyclyloxy, optionally substituted pyridinium, or —N(OCH$_3$)CH$_3$.

The term "amide bond" as used herein, refers to a covalent bond between a nitrogen atom and a carbon atom in a carbonyl group.

The term "amide linkage" as used herein, refers to a connection between two carbon atoms of the type —C—C(O)NH—C—.

The term "amide bond forming coupling reagent" or "coupling agent" as used herein, refers to an inorganic or organic compound used to facilitate the formation of an amide bond. It may include a coupling additive, used in combination with another coupling reagent to speed up coupling process and inhibit side reactions.

The term "coupling additive" as used herein, refers to the coupling reagents that, in addition to facilitating the formation of amide bond, also inhibit side reactions and reduce racemization. Non-limiting examples of coupling additives include N-hydroxysuccinimide (HOSu), N-hydroxy-5-norbornene-2,3-dicarboximide (HONB), 1-hydroxybenzotriazole (HOBt), 6-chloro-1-hydroxybenzotriazole (6-Cl-HOBt), 1-hydroxy-7-azabenzotriazole (HOAt), 3-hydroxy-4-oxo-3,4-dihydro-1,2,3-benzotriazine (HODhbt), its aza derivative (HODhat), and 2-pyridinol 1-oxide (HOPO).

The term "strong acid" as used herein, refers to any acid whose pK$_a$ is less than or equal to 3, preferably less than or equal to 0, more preferably less than or equal to −3, as defined herein. Non-limiting examples of the strong acid includes mineral acid such as sulfuric acid, phosphoric acid, nitric acid, and hydrochloric acid; or a strong organic acid such as methane sulfonic acid, ethane sulfonic acid, propane sulfonic acid, butane sulfonic acid, xylene sulfonic acid, and benzene sulfonic acid.

The term "nitrite salts" as used herein, refers to a nitrite anion-containing compounds and salt forms thereof. Non-limiting examples of the nitrite salts include sodium nitrite, potassium nitrite or magnesium nitrite.

The term "nanomaterial" as used herein, unless otherwise is indicated or is clear from the context, refers to materials with physical phenomena, structural features and/or construct structures that typically have at least one dimension measuring in nanoscale range, preferably from about 1.0 nanometer (nm), more preferably about 0.1 nm, up to about 100 nm, up to about 130 nm, up to about 200 nm, desirably up to about 350 nm, more desirably up to about 500 nm, preferably up to about 600 nm, more preferably up to about 750 nm, most desirably up to about 850 nm, and most preferably up to about 1000 nm. The term "nanomaterial" as used herein, includes, but is not limited to functionalized and solubilized multi-walled carbon, single-walled carbon nanotube.

The term "nanotube" as used herein, unless otherwise is indicated or is clear from the context, refers to a tubular, strand-like structure that has a circumference measuring in nanoscale range, preferably from about 1.0 nm, more preferably about 0.1 nm, up to about 100 nm, up to about 130 nm, up to about 200 nm, desirably up to about 350 nm, more desirably up to about 500 nm, preferably up to about 600 nm, more preferably up to about 750 nm, most desirably up to about 850 nm, and most preferably up to about 1000 nm.

The term "carbon nanotube" or "CNT" or "CNTs" as used herein, unless otherwise is indicated or is clear from the context, refers to any type of carbon nanotube. Carbon nanotubes typically exist as single layers or multiple layers of cylindrical layers of graphene sheets. The individual sheets may vary in layering, and functionality. In addition, the carbon nanotubes may take a variety of known morphologies, such as those chosen from nanohoms, cylinders, nanospirals, dendrites, spider nanotube structures, Y-junction nanotubes, nanorods, and bamboo morphology. For example, carbon nanotube may exist as single-walled carbon nanotube and multi-walled carbon nanotube. Further, the carbon nanotube may be conductive, semi-conductive, or insulated. Carbon nanotube may also be chiral or achiral.

The term "functionalized carbon nanotube" as used herein, unless otherwise is indicated or is clear from the context, refers to a carbon nanotube to which has been bound a substituent. A carbon nanotube may be functionalized by an organic, organometallic or inorganic substituent. In a non-limiting example the substituents are located on the ends of the carbon nanotubes and are optionally polymerized. In a further non-limiting example the functionalized carbon nanotubes may comprise a uniformity or non-uniformity in composition and/or density of functionalization across the surface of the carbon nanotubes.

The term "single-walled carbon nanotube" or "SWCNT" or "SWCNTs" as used herein, unless otherwise is indicated or is clear from the context, refers to cylindrically shaped thin sheet of carbon atoms having a wall consisting essentially of a single layer of carbon atoms, and arranged in a hexagonal crystalline structure with a graphitic type of bonding.

The term "multi-walled carbon nanotube" or "MWCNT" or "MWCNTs" as used herein, unless otherwise is indicated or is clear from the context, refers to a nanotube composed of more than one concentric tube.

The term "solution" as used herein, refers to its normal meaning, as understood by one skilled in the art—i.e., homogeneous mixture of a solid dissolved in a liquid. However, as used herein, the term "solution" is not intended to be read as necessarily requiring the absence of other, non-dissolved materials, or a that the solution is the continuous phase of a mixture.

The term "mixture" as used herein, refers to a physical aggregate or a mechanical aggregate, or three or more individual, chemically distinct that are not chemically bound. The term mixture is intended to encompass combinations.

The term "aqueous solution" as used herein, refers to a liquid having a relatively high polarity and being substantially immiscible with oils.

The term "pollutant" as used herein, refers to any substance the release of which is either legally regulated or is generally known to be harmful to human health and the environment, either directly through toxic effects or indirectly, whether a substance is a pollutant is partially determined by extrinsic properties, such as the amount of the substance. The pollutant may be human made, but at the same time natural products may also be pollutants.

The term "contacting" as used herein, refers to any suitable way of contacting the aqueous solution as described herein with the nanomaterial as described herein. Non-limiting example of contacting includes a simple addition of the nanomaterial to the aqueous solution with or without mixing.

The term "ion" as used herein, refers to any molecule, portion of a molecule, cluster of molecules, molecular complex, moiety, or atom that contains a charge (positive, negative, or both (e.g., Zwitterions) or that may be made to contain a charge.

The term "heavy metal" as used herein, refers to a metal, metalloid, lanthanides, or actinides with a large atomic number (no strict and/or unique scientific definitions though). Examples of "heavy metals" include, but are not limited to zirconium, hafnium, chromium, zinc, copper, cadmium, lead, mercury, manganese, and so on. The term "heavy metal", unless otherwise is indicated or is clear from the context includes heavy metal ion.

The term "organic dye" as used herein, unless otherwise is indicated or is clear from the context, refers to any pigment that satisfies the definition of a chapter on organic pigments in Ullmann's encyclopedia [Hunger, K. et al. "Pigments, Organic", Ullmann's Encyclopedia of Industrial Chemistry 27, 380-423, 2012; Jaffe, E. E. "Pigments, Organic", Kirk-Othmer Encyclopedia of Chemical Technology 19, 417-456, 2004].

In an embodiment, the present invention relates to a nanomaterial formed by a reaction of a functionalized carbon nanotube comprising first and second aminoalkyl groups covalently bonded to a surface of the carbon nanotube and a porphyrin ring of formula (I)

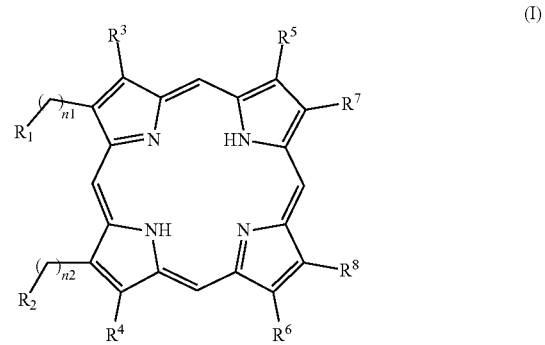

or a salt thereof, a solvate thereof, a tautomer thereof, a stereoisomer thereof, a metalation product thereof, or a mixture thereof, wherein the first and second aminoalkyl groups are each independently a $C_{1-6}$ alkyl substituted with at least one primary or secondary amino group, $R_1$ and $R_2$ are independently —COOH or an activated carbonyl group, $R_3$, $R_4$, $R_5$, $R_6$, $R_7$, and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl, $n_1$ and $n_2$ are independently an integer in a range of 1-6 and the functionalized carbon nanotube is bonded with the porphyrin ring of formula (I) via two amide linkages, one formed between $R_1$ of the porphyrin ring and the first aminoalkyl group of the functionalized carbon nanotube, and the other between $R_2$ of the porphyrin ring and the second aminoalkyl group of the functionalized carbon nanotube.

Another embodiment of the present invention relates to the nanomaterial formed by the reaction of the functionalized carbon nanotube comprising first and second aminoalkyl groups covalently bonded to a surface of the carbon nanotube and a porphyrin ring of the formula (I) or a salt thereof, a solvate thereof, a tautomer thereof, a stereoisomer thereof, a metalation product thereof, or a mixture thereof.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the first and second aminoalkyl groups are each independently a $C_{1-6}$ alkyl substituted with at least one primary or secondary amino group.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_1$ and $R_2$ are independently —COOH or an activated carbonyl group.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $n_1$ and $n_2$ are independently an integer in a range of 1-6.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_3$ and $R_4$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_5$ and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_6$ and Ry are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl.

Yet another embodiment of the present invention relates to the nanomaterial formed by the reaction of the functionalized carbon nanotube comprising first and second aminoalkyl groups covalently bonded to a surface of the carbon nanotube and a porphyrin ring of formula (I)

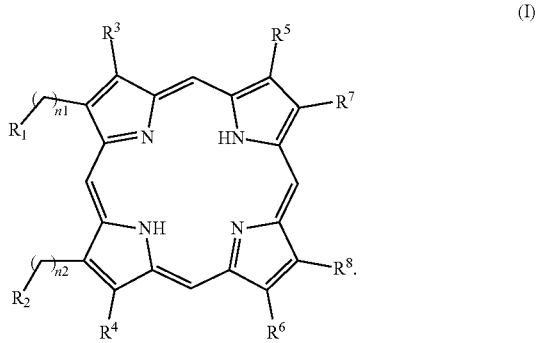

Yet another embodiment of the present invention relates to the nanomaterial formed by the reaction of the functionalized carbon nanotube comprising first and second aminoalkyl groups covalently bonded to a surface of the carbon nanotube and a porphyrin ring of formula (I)

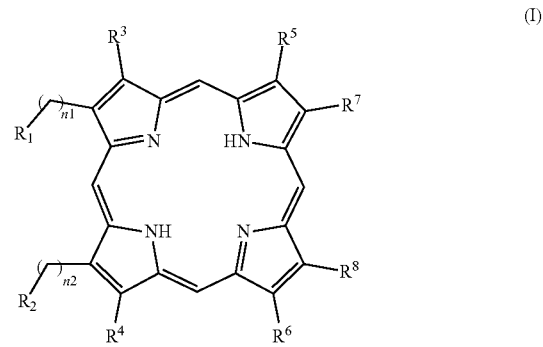

or a metalation product thereof.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein a shortest distance between the first and second aminoalkyl groups on the surface of the functionalized carbon nanotube is about 0.1-20 nm.

In an embodiment, the present invention relates to the nanomaterial formed by the reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein the functionalized carbon nanotube is a multi-walled carbon nanotube.

Another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the functionalized carbon nanotube is the multi-walled carbon nanotube.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the first and second aminoalkyl groups are each independently a $C_{1-6}$ alkyl substituted with at least one primary or secondary amino group and the functionalized carbon nanotube is the multi-walled carbon nanotube.

Yet another embodiment of the present invention relates to the nanomaterial formed by the reaction of the functionalized carbon nanotube comprising first and second aminoalkyl groups covalently bonded to a surface of the carbon nanotube and a porphyrin ring of formula (I)

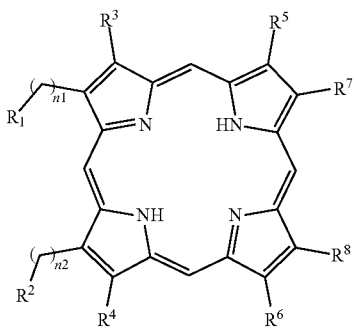

wherein the functionalized carbon nanotube is the multi-walled carbon nanotube, $R_1$ and $R_2$ are independently —COOH or an activated carbonyl group, $R_3$, $R_4$, $R_5$, $R_6$, $R_7$, and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl, $n_1$ and $n_2$ are independently an integer in a range of 1-6 and the functionalized carbon nanotube is bonded with the porphyrin ring of formula (I) via two amide linkages, one formed between $R_1$ of the porphyrin ring and the first aminoalkyl group of the functionalized carbon nanotube, and the other between $R_2$ of the porphyrin ring and the second aminoalkyl group of the functionalized carbon nanotube.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein the first and second aminoalkyl groups are —$CH_2CH_2NH_2$.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the first and second aminoalkyl groups are —$CH_2CH_2NH_2$.

Yet another embodiment of the present invention relates to the nanomaterial formed by the reaction of the functionalized carbon nanotube comprising first and second aminoalkyl groups covalently bonded to a surface of the carbon nanotube and a porphyrin ring of formula (I)

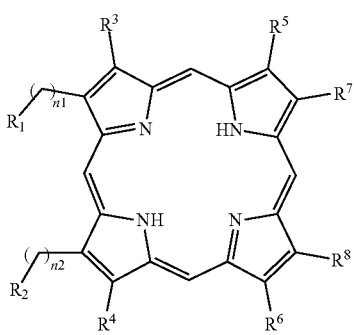

wherein the first and second aminoalkyl groups are —$CH_2CH_2NH_2$, $R_1$ and $R_2$ are independently —COOH or an activated carbonyl group, $R_3$, $R_4$, $R_5$, $R_6$, $R_7$, and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl, $n_1$ and $n_2$ are independently an integer in a range of 1-6 and the functionalized carbon nanotube is bonded with the porphyrin ring of formula (I) via two amide linkages, one formed between $R_1$ of the porphyrin ring and the first aminoalkyl group of the functionalized carbon nanotube, and the other between $R_2$ of the porphyrin ring and the second aminoalkyl group of the functionalized carbon nanotube.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the first and second aminoalkyl groups are —$CH_2CH_2NH_2$ and the functionalized carbon nanotube is the multi-walled carbon nanotube.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_1$ and $R_2$ are —COOH.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, $R_1$ and $R_2$ are —COOH.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the first and second aminoalkyl groups are —$CH_2CH_2NH_2$, $R_1$ and $R_2$ are —COOH.

Yet another embodiment of the present invention relates to the nanomaterial formed by the reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, the first and second aminoalkyl groups are —$CH_2CH_2NH_2$ and $R_1$ and $R_2$ are —COOH.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $n_1$ and $n_2$ are 1.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $n_1$ and $n_2$ are 1.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, $n_1$ and $n_2$ are 1.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the first and second aminoalkyl groups are —$CH_2CH_2NH_2$, $n_1$ and $n_2$ are 1.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $n_1$ and $n_2$ are 1.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, the first and second aminoalkyl groups are —$CH_2CH_2NH_2$, $R_1$ and $R_2$ are —COOH, $n_1$ and $n_2$ are 1.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_3$ and $R_4$ are —$CH_3$.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_3$ and $R_4$ are —$CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the first and second aminoalkyl groups are —$CH_2CH_2NH_2$, $R_3$ and $R_4$ are —$CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $R_3$ and $R_4$ are —$CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $n_1$ and $n_2$ are 1, $R_3$ and $R_4$ are —$CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, the first and second aminoalkyl groups are —$CH_2CH_2NH_2$, $R_1$ and $R_2$ are —COOH, $R_3$ and $R_4$ are —$CH_3$.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_5$ and $R_8$ are independently —$CH_3$ or —CH—$CH_2$.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_5$ and $R_8$ are independently —$CH_3$ or —CH=$CH_2$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $R_5$ and $R_8$ are independently —$CH_3$ or —CH=$CH_2$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_3$ and $R_4$ are —$CH_3$, $R_5$ and $R_8$ are independently —$CH_3$ or —CH—$CH_2$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $R_3$ and $R_4$ are —$CH_3$, $R_5$ and $R_8$ are independently —$CH_3$ or —CH=$CH_2$, $n_1$ and $n_2$ are 1.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, $R_1$ and $R_2$ are —COOH, $R_3$ and $R_4$ are $CH_3$, $R_5$ and $R_8$ are independently —$CH_3$ or —CH=$CH_2$.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein $R_6$ and $R_7$ are independently —$CH_3$ or —CH(OH)$CH_3$.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_6$ and $R_7$ are independently —$CH_3$ or —CH(OH)$CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $R_3$ and $R_4$ are —$CH_3$, $R_6$ and $R_7$ are independently —$CH_3$ or —$CH(OH)CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein $R_1$ and $R_2$ are —COOH, $R_3$ and $R_4$ are —$CH_3$, $R_5$ and $R_8$ are independently —$CH_3$ or —$CH=CH_2$, $R_6$ and $R_7$ are independently —$CH_3$ or —$CH(OH)CH_3$.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, $R_6$ and $R_7$ are independently —$CH_3$ or —$CH(OH)CH_3$.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I), wherein the porphyrin ring is

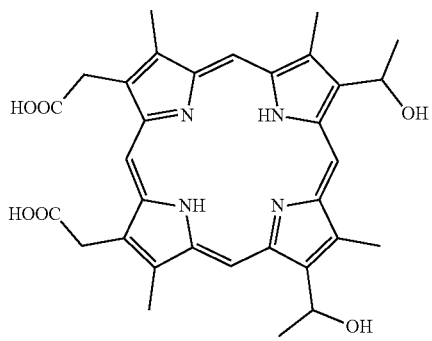 [SMILES: CC1=C(CC(=O)O)c2cc3[nH]c(cc4nc(cc5[nH]c(cc1n2)c(C)c5C(C)O)C(C)=C4C(C)O)c(C)c3CC(=O)O]

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube and the porphyrin ring is

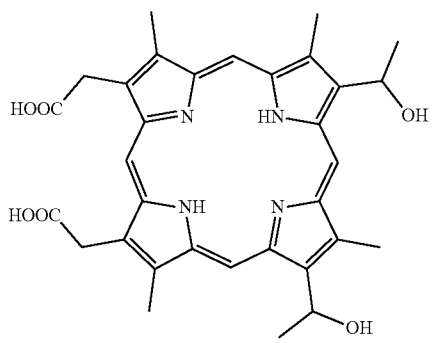 [SMILES: CC1=C(CC(=O)O)c2cc3[nH]c(cc4nc(cc5[nH]c(cc1n2)c(C)c5C(C)O)C(C)=C4C(C)O)c(C)c3CC(=O)O]

In a specific embodiment of the present invention relates to the nanomaterial formed by a reaction of the functionalized carbon nanotube comprising first and second aminoalkyl groups covalently bonded to a surface of the carbon nanotube and the porphyrin ring of formula (I), wherein the functionalized carbon nanotube is a multi-walled carbon nanotube, the first and second aminoalkyl groups are —$CH_2CH_2NH_2$ and the porphyrin ring is

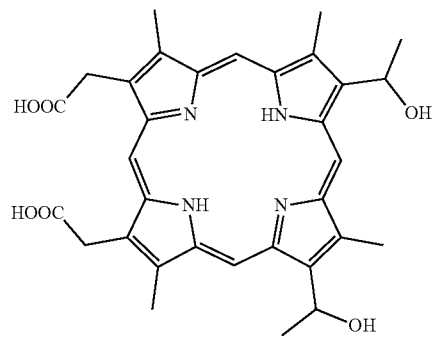 [SMILES: CC1=C(CC(=O)O)c2cc3[nH]c(cc4nc(cc5[nH]c(cc1n2)c(C)c5C(C)O)C(C)=C4C(C)O)c(C)c3CC(=O)O]

In an embodiment, the present invention relates to the nanomaterial formed by a reaction of the functionalized carbon nanotube comprising first and second aminoalkyl groups covalently bonded to a surface of the carbon nanotube and metalation product of porphyrin ring of formula (I), wherein the metalation product of porphyrin ring of formula (I) is of formula (II)

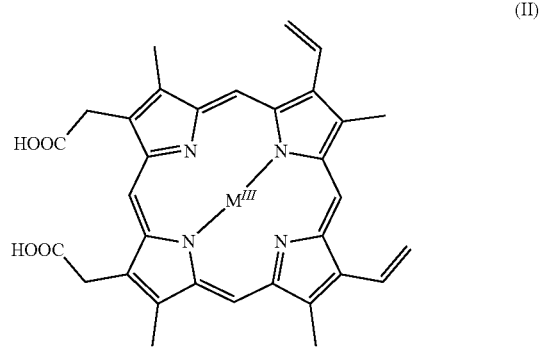

(II)

wherein M is a metal selected from the group consisting of Mn, Fe, and Co.

Another embodiment of the present invention relates to the nanomaterial formed by a reaction of the functionalized carbon nanotube comprising first and second aminoalkyl groups covalently bonded to a surface of the carbon nanotube and metalation product of porphyrin ring of formula (I), wherein the functionalized carbon nanotube is a multi-walled carbon nanotube, the metalation product of porphyrin ring of formula (I) is of formula (II)

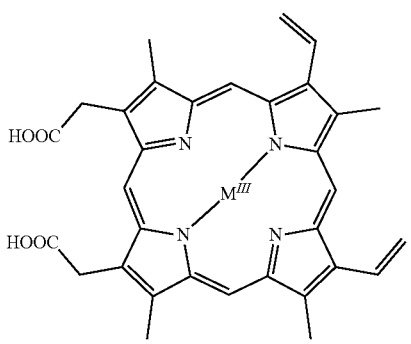

wherein M is a metal selected from the group consisting of Mn, Fe, and Co.

Yet another embodiment of the present invention relates to the nanomaterial formed by a reaction of the functionalized carbon nanotube comprising first and second aminoalkyl groups covalently bonded to a surface of the carbon nanotube and metalation product of porphyrin ring of formula (I), wherein the functionalized carbon nanotube is a multi-walled carbon nanotube, the first and second aminoalkyl groups are —CH$_2$CH$_2$NH$_2$ and the metalation product of porphyrin ring of formula (I) is of formula (II)

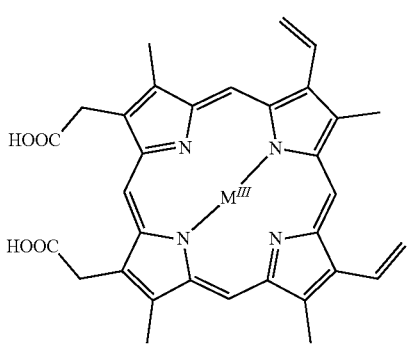

(II)

wherein M is a metal selected from the group consisting of Mn, Fe, and Co.

In an embodiment, the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein a shortest distance between the first and second aminoalkyl groups on the surface of the functionalized carbon nanotube is about 0.1-10 nm.

Another embodiment of the present invention relates to the nanomaterial formed by a reaction of the functionalized carbon nanotube comprising first and second aminoalkyl groups covalently bonded to a surface of the carbon nanotube and the porphyrin ring of formula (I) wherein the shortest distance between the first and second aminoalkyl groups on the surface of the functionalized carbon nanotube is about 0.1-10 nm.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) wherein the shortest distance between the first and second aminoalkyl groups on the surface of the functionalized carbon nanotube is about 0.1-10 nm, preferably more than about 0.2 nm, more preferably about 0.5 nm, most preferably about 0.8 nm, up to about 9 nm, more preferably up to about 8 nm, most preferably up to about 6 nm.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) wherein R$_6$ and R$_7$ are independently —CH$_3$ or —CH(OH)CH$_3$ and the shortest distance between the first and second aminoalkyl groups on the surface of the functionalized carbon nanotube is about 0.1-10 nm.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) wherein the functionalized carbon nanotube is a multi-walled carbon nanotube and the shortest distance between the first and second aminoalkyl groups on the surface of the functionalized carbon nanotube is about 0.1-10 nm.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) wherein the first and second aminoalkyl groups are —CH$_2$CH$_2$NH$_2$ and the shortest distance between the first and second aminoalkyl groups on the surface of the functionalized carbon nanotube is about 0.1-10 nm.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein density of functionalization vary ranging from about 0.1% to 10%.

Yet another embodiment of the present invention relates to the nanomaterial formed by a reaction of the functionalized carbon nanotube comprising first and second aminoalkyl groups covalently bonded to a surface of the carbon nanotube and the porphyrin ring of formula (I) or a salt thereof, a solvate thereof, a tautomer thereof, a stereoisomer thereof, a metalation product thereof, or a mixture thereof, wherein density of functionalization vary ranging from about 0.1 to 10%, preferably from about 0.5%, more preferably about 1%, most preferably about 2%, up to about 8%, more preferably up to about 6%, most preferably up to about 4%.

In an embodiment, the present invention also relates to a method of preparing the nanomaterial, the method comprises mixing the functionalized carbon nanotube with the porphyrin ring of formula (I) thereby forming the nanomaterial.

Another embodiment of the present invention relates to a method of preparing the nanomaterial, the method comprises mixing the functionalized carbon nanotube with the porphyrin ring of formula (I) or a salt thereof, a solvate thereof, a tautomer thereof, a stereoisomer thereof, a metalation product thereof, or a mixture thereof, thereby forming the nanomaterial.

Yet another embodiment of the present invention relates to a method of preparing the nanomaterial, the method comprises mixing the functionalized carbon nanotube with the porphyrin ring of formula (I) thereby forming the nanomaterial, wherein the functionalized carbon nanotube comprises first and second aminoalkyl groups covalently bonded to surface of the carbon nanotube.

Yet another embodiment of the present invention relates to a method of preparing the nanomaterial, the method comprises mixing the functionalized carbon nanotube with the porphyrin ring of formula (I) thereby forming the nanomaterial, wherein the functionalized carbon nanotube is a multi-walled carbon nanotube.

Yet another embodiment of the present invention relates to a method of preparing the nanomaterial, the method comprises mixing the functionalized carbon nanotube with the porphyrin ring of formula (I) thereby forming the nanomaterial, wherein the functionalized carbon nanotube comprises first and second aminoalkyl groups covalently bonded to surface of the carbon nanotube, and wherein the first and second aminoalkyl groups are —$CH_2CH_2NH_2$.

In an embodiment, the present invention relates to the method of preparing the nanomaterial, the method comprises mixing the functionalized carbon nanotube with the porphyrin ring of formula (I) thereby forming the nanomaterial, wherein $R_1$ and $R_2$ are —COOH, and wherein the mixing occurs in the presence of an amide bond formation coupling reagent.

Another embodiment of the present invention relates to the method of preparing the nanomaterial, the method comprises mixing the functionalized carbon nanotube with the porphyrin ring of formula (I) or a salt thereof, a solvate thereof, a tautomer thereof, a stereoisomer thereof, a metalation product thereof, or a mixture thereof, thereby forming the nanomaterial, wherein $R_1$ and $R_2$ are —COOH, and wherein the mixing occurs in the presence of an amide bond formation coupling reagent.

Yet another embodiment of the present invention relates to the method of preparing the nanomaterial, the method comprises mixing the functionalized carbon nanotube with the porphyrin ring of formula (I), thereby forming the nanomaterial, wherein the functionalized carbon nanotube comprises first and second aminoalkyl groups covalently bonded to surface of the carbon nanotube, $R_1$ and $R_2$ are —COOH, and wherein the mixing occurs in the presence of an amide bond formation coupling reagent.

Yet another embodiment of the present invention relates to a method of preparing the nanomaterial, the method comprises mixing the functionalized carbon nanotube with the porphyrin ring of formula (I) thereby forming the nanomaterial, wherein the functionalized carbon nanotube is a multi-walled carbon nanotube, $R_1$ and $R_2$ are —COOH, and wherein the mixing occurs in the presence of an amide bond formation coupling reagent.

Yet another embodiment of the present invention relates to a method of preparing the nanomaterial, the method comprises mixing the functionalized carbon nanotube with the porphyrin ring of formula (I) thereby forming the nanomaterial, wherein the first and second aminoalkyl groups are —$CH_2CH_2NH_2$, $R_1$ and $R_2$ are —COOH, and wherein the mixing occurs in the presence of an amide bond formation coupling reagent.

In an embodiment, the present invention relates to the method of preparing the nanomaterial, the method comprises mixing the functionalized carbon nanotube with the porphyrin ring of formula (I) thereby forming the nanomaterial, wherein the first and second aminoalkyl groups are —$CH_2CH_2NH_2$, and the amine functionalized carbon nanotube is prepared by mixing a carbon nanotube with ethylene diamine in the presence of a nitrite salt and a strong acid.

Another embodiment of the present invention relates to the method of preparing the nanomaterial, the method comprises mixing the functionalized carbon nanotube with the porphyrin ring of formula (I) or a salt thereof, a solvate thereof, a tautomer thereof, a stereoisomer thereof, a metalation product thereof, or a mixture thereof, thereby forming the nanomaterial, wherein the first and second aminoalkyl groups are —$CH_2CH_2NH_2$, and the amine functionalized carbon nanotube is prepared by mixing the carbon nanotube with ethylene diamine in the presence of a nitrite salt and a strong acid.

Yet another embodiment of the present invention relates to the method of preparing the nanomaterial, the method comprises mixing the functionalized carbon nanotube with the porphyrin ring of formula (I) or a salt thereof, a solvate thereof, a tautomer thereof, a stereoisomer thereof, a metalation product thereof, or a mixture thereof, thereby forming the nanomaterial, wherein the first and second aminoalkyl groups are $CH_2CH_2NH_2$, and the amine functionalized carbon nanotube is prepared by mixing multi-walled carbon nanotube with ethylene diamine in the presence of a nitrite salt and a strong acid.

In an embodiment, the present invention also relates to a method for removing a pollutant from an aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the initial concentration of the pollutant in the aqueous solution is in a range of about 10 to 1000 mg $L^{-1}$, the nanomaterial is present in a concentration ranging from about 0.001 to 10 g per liter of the aqueous solution during the contacting and the nanomaterial is contacted with the aqueous solution at a temperature in a range of about 10° C. to 80° C. for about 0.1 to 24 hours.

Another embodiment of the present invention also to a method for removing a pollutant from an aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the initial concentration of the pollutant in the aqueous solution is in a range of about 10 to, 000 mg $L^{-1}$, preferably more than about 20 mg $L^{-1}$, more preferably about 30 mg $L^{-1}$, most preferably about 50 mg $L^{-1}$, up to about 900 mg $L^{-1}$, more preferably up to about 800 mg $L^{-1}$, most preferably up to about 500 mg $L^{-1}$.

Yet another embodiment of the present invention also relates to a method for removing a pollutant from an aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the initial concentration of the pollutant in the aqueous solution is in a range of about 10 to 1000 mg $L^{-1}$, the nanomaterial is present in a concentration ranging from about 0.001 to 10 g per liter of the aqueous solution during the contacting, preferably more than about 0.01 g per liter, more preferably about 0.1 g per liter, most preferably about 1 g per liter, up to about 9 g per liter, more preferably up to about 8 g per liter, most preferably up to about 5 g per liter.

Yet another embodiment of the present invention also relates to a method for removing a pollutant from an aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the initial concentration of the pollutant in the aqueous solution is in a range of about 10 to 1000 mg $L^{-1}$, the nanomaterial is present in a concentration ranging from about 0.001 to 10 g per liter of the aqueous solution during the contacting and the nanomaterial is contacted with the aqueous solution at a temperature in a range of about 10° C. to 80° ° C., preferably from about 15° C., more preferably about 20° C., most preferably about 25° C., up to about 75° C., more preferably up to about 70° ° C., most preferably up to about 65° C.

Yet another embodiment of the present invention also relates to a method for removing a pollutant from an aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the initial concentration of the pollutant in the aqueous solution is in a range of about 10 to 1000 mg $L^{-1}$, the nanomaterial is present in a concentration ranging from about 0.001 to 10 g per liter of the aqueous solution during the contacting and the nanomaterial is contacted with the aqueous solution at a temperature in a range of about 10° C. to 80° C., for about 0.1 to 24 hours, preferably from about 0.5 hour, more preferably about 1 hour, most preferably about 5 hours, up to about 22 hours, more preferably up to about 20 hours, most preferably up to about 18 hours.

In an embodiment, the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is an organic dye, a heavy metal, or both.

Another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is the organic dye.

Yet another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is the heavy metal.

Yet another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is a combination of the organic dye and the heavy metal.

In an embodiment, the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is an organic dye and wherein the organic dye is methylene blue.

In an embodiment, the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the pollutant is a heavy metal, and wherein the heavy metal is an ion of at least one heavy metal selected from the group consisting of Ni, Cd, Pb, As, Cr, Cu, and Fe.

In an embodiment, the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the aqueous solution has a pH in a range of about 3 to 7.

Another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein the aqueous solution has a pH in a range of about 3 to 7, preferably more than about 3.5, more preferably about 4, most preferably about 5, up to about 6.5, more preferably up to about 6, most preferably up to about 6.

In an embodiment, the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein greater than about 75% of a total mass of the pollutant is removed from the aqueous solution.

Another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein greater than about 85% of a total mass of the pollutant is removed from the aqueous solution.

Yet another embodiment of the present invention relates to the method for removing a pollutant from aqueous solution, the method comprises contacting the aqueous solution having an initial concentration of the pollutant with the nanomaterial to form a mixture and filtering the mixture to obtain an aqueous solution having a reduced concentration of the pollutant compared to the initial concentration, wherein up to about 100% of a total mass of the pollutant is removed from the aqueous solution.

EXAMPLES

Example 1a: Synthesis of Amine Functionalized Carbon Nanotube (1)

MWCNTs (70 mg, 5.8 millimole (mmol) of C) were added into a mixture of sodium nitrite (NaNO$_2$) (930 mg, 1.40 mmol) and ethylene diamine (85.0 mg, 1.40 mmol), followed by slow addition of concentrated H$_2$SO$_4$ (0.0610 mL, 1.20 mmol). The reaction mixture was then kept under heating for 1 hour at 60° C. Afterwards, the reaction mixture was cooled and diluted with dimethylformamide (DMF) followed by mixing and centrifuging. The obtained product was rinsed with DMF followed by water to eliminate any unreacted ethylene diamine. FIG. 1 shows a scheme for synthesis of amine functionalized carbon nanotube (1) from MWCNT and ethylene diamine.

Example 1b: Synthesis of chloro(protoporphyrinato)iron(III)-MWCNTs Linked (2)

Figure 2:
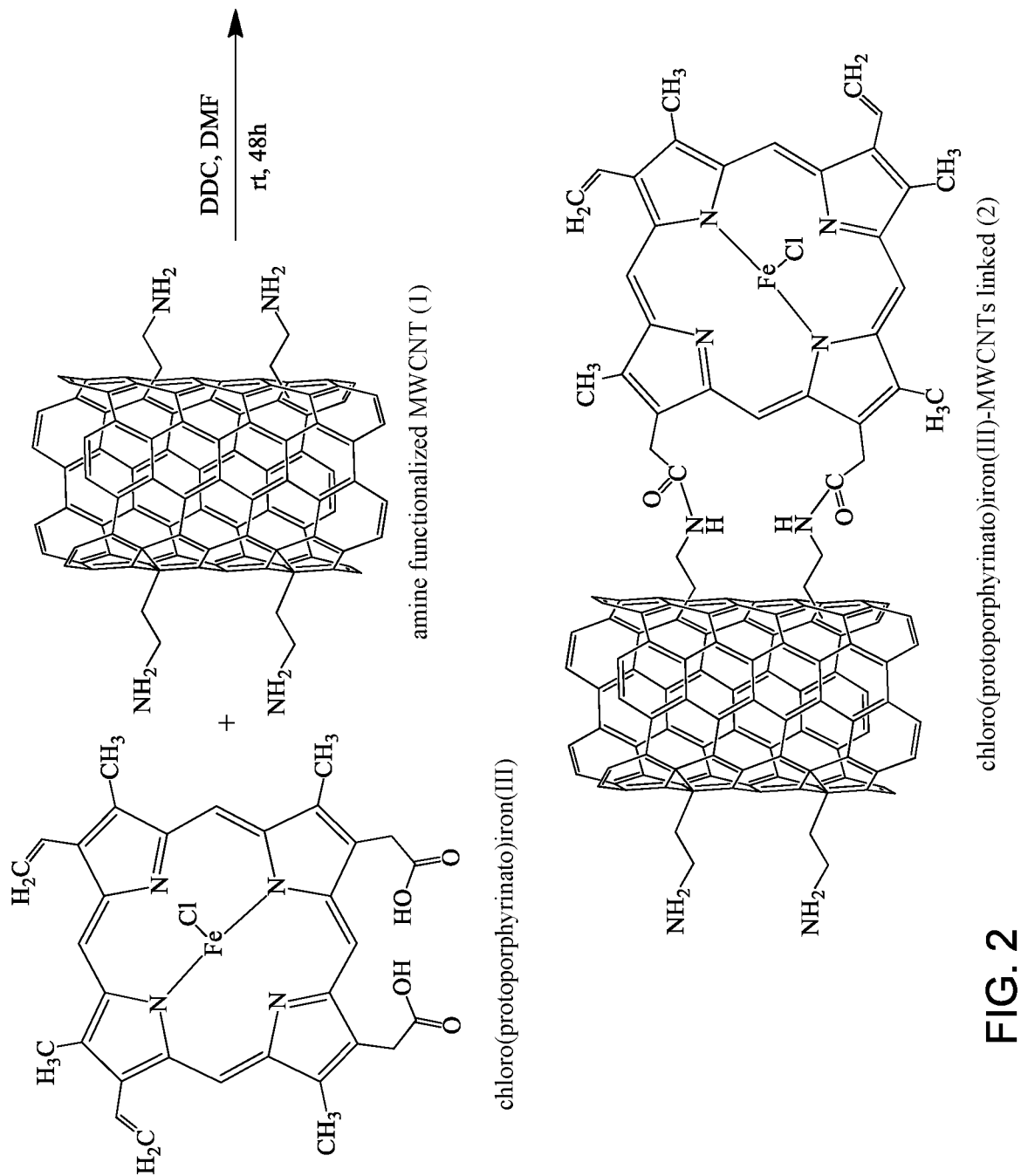
FIG. 2 is a scheme for synthesis of chloro(protoporphyrinato)iron(III)-MWCNTs linked (2).

Chloro(protoporphyrinato)iron(III) (10.4 mg, 0.010 mmol) was dissolved in DMF (10.0 mL) and dicyclohexyl carbodiimide (DCC) (32.9 mg, 0.160 mmol) was added to convert carboxylic groups (—COOH) to active carbodiimide ester groups. The reaction mixture was stirred under nitrogen atmosphere at room temperature for one day. Thereafter, the amine functionalized carbon nanotube (1) (10.0 mg, 0.830 mmol of C) was added and the reaction mixture was stirred for two days. The solid product was extracted and rinsed with DMF to eliminate unreacted chloro(protoporphyrinato)iron(III) and DCC intermediates. The product was dried at 70° C. to obtain a dark black-green powder of chloro(protoporphyrinato)iron(III)-MWCNTs linked (2). FIG. 2 shows a scheme for synthesis of chloro(protoporphyrinato)iron(III)-MWCNTs linked (2) from amine functionalized carbon nanotube (1) and chloro(protoporphyrinato)iron(III).

Example 1c: Synthesis of 8,13-bis(1-hydroxyethyl)-3,7,12,17-tetramethyl-21H,23H-porphine-2,18-dipropionic Acid-MWCNTs Linked (3)

Figure 3:
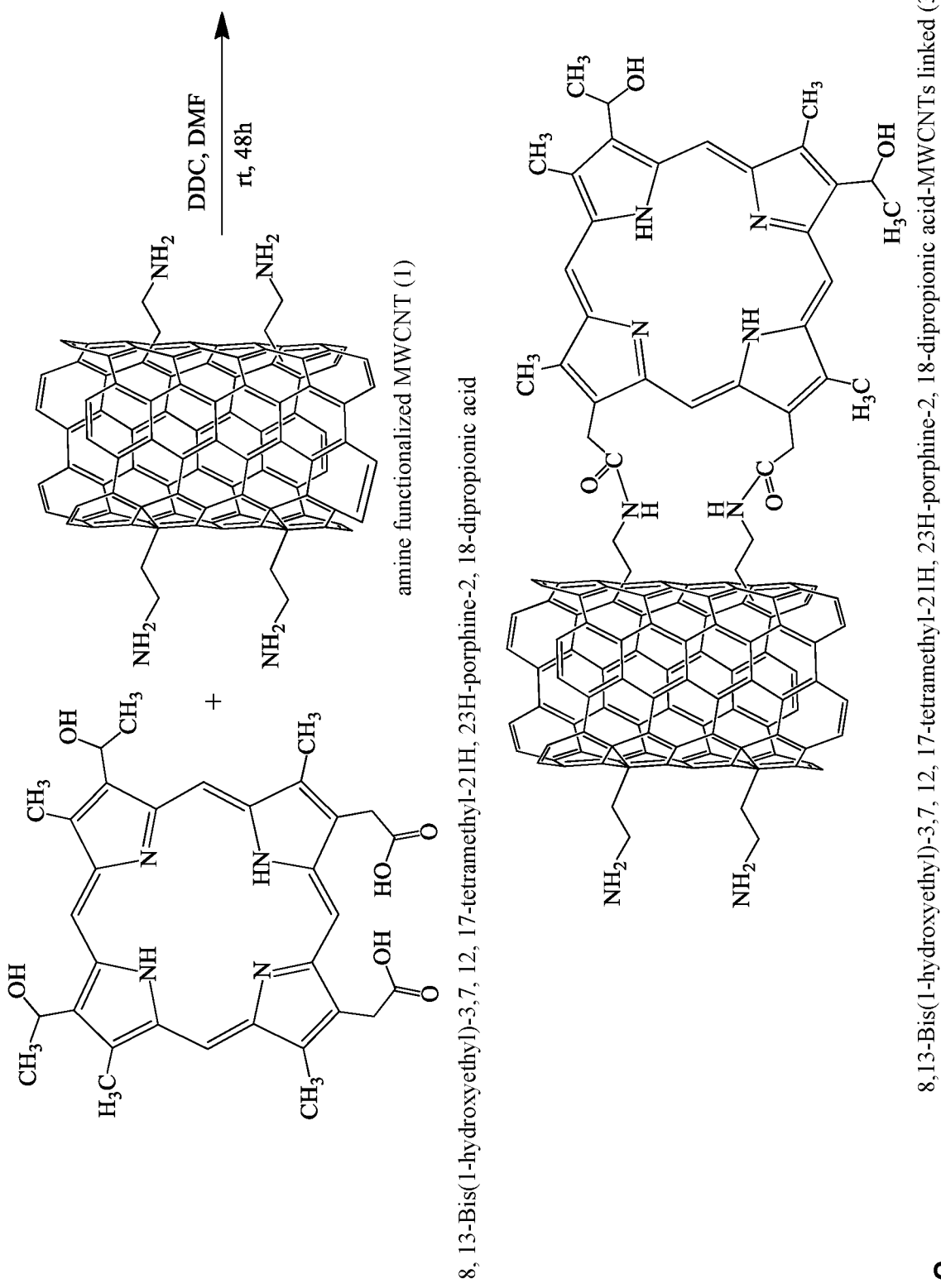
FIG. 3 is a scheme for synthesis of 8,13-Bis(1-hydroxyethyl)-3,7,12,17-tetramethyl-21H,23H-porphine-2,18-dipropionic acid-MWCNTs linked (3).

8,13-Bis(1-hydroxyethyl)-3,7,12,17-tetramethyl-21H,23H-porphine-2,18-dipropionic acid (10.4 mg, 0.010 mmol) was dissolved in 10 mL of DMF and DCC (32.9 mg, 0.160 mmol) was added to convert carboxylic groups (—COOH) to active carbodiimide ester groups. The reaction mixture was stirred under nitrogen atmosphere at room temperature for one day. Thereafter, the functionalized carbon nanotube (1) (10.0 mg, 0.830 mmol of C) was added and the reaction mixture was stirred for two days. The solid product was extracted and rinsed with DMF to eliminate unreacted components. The product was dried to obtain a dark black-green powder of 8,13-bis(1-hydroxyethyl)-3,7,12,17-tetramethyl-21H,23H-porphine-2,18-dipropionic acid-MWCNTs linked (3). FIG. 3 shows a scheme for synthesis of 8,13-bis(1-hydroxyethyl)-3,7,12,17-tetramethyl-21H,23H-porphine-2,18-dipropionic acid-MWCNTs linked (3) from amine functionalized carbon nanotube (1) and 8,13-bis(1-hydroxyethyl)-3,7,12,17-tetramethyl-21H,23H-porphine-2,18-dipropionic acid.

Example 2: Influence of pH on Removal Efficiency of the Nanomaterial

Initial pH of methylene blue solution was varied under constant experimental conditions to study the removal efficiency of chloro(protoporphyrinato)iron(III)-MWCNTs linked (nanomaterial 2), 8,13-bis(1-hydroxyethyl)-3,7,12,17-tetramethyl-21H,23H-porphine-2,18-dipropionic acid-MWCNTs linked (nanomaterial 3) and amine functionalized carbon nanotube (1) for removal of methylene blue from aqueous solution.

Methylene blue removal efficiency was calculated by equation (1):

$$\text{methylene blue dye removal efficiency (\%)} = \frac{(c_i - c_e)}{c_i} \times 100 \quad (1)$$

where, $C_i$ and $C_e$ stand for initial as well as equilibrium concentrations of methylene blue.

Figure 4:
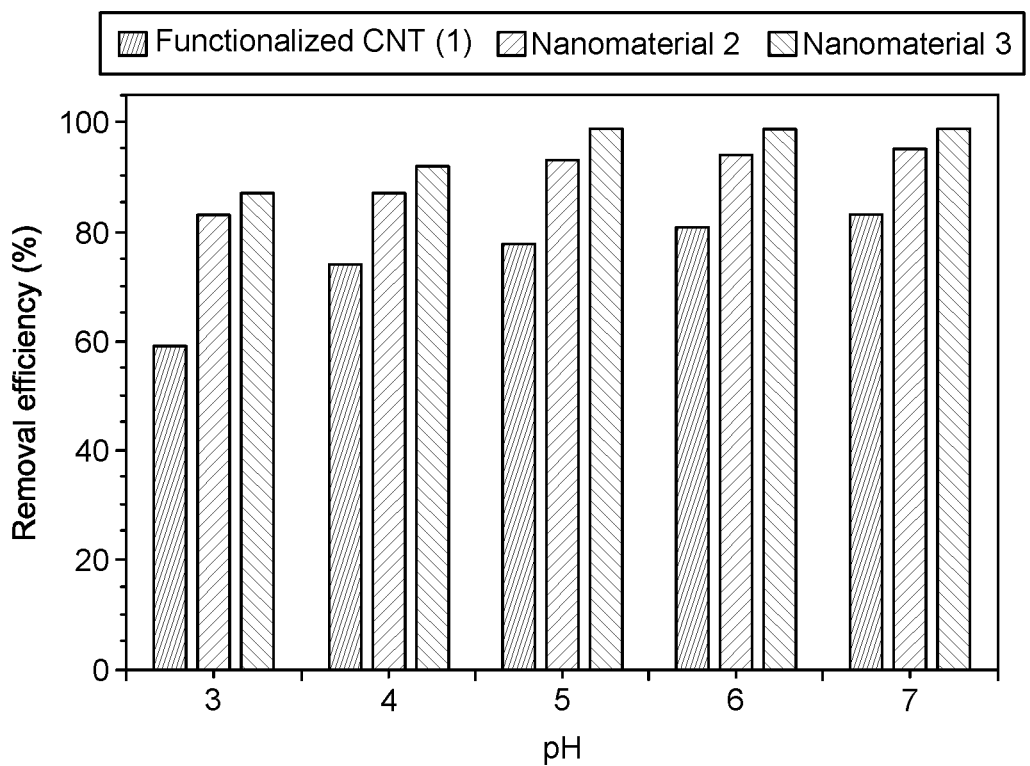
FIG. 4 is a graphical representation showing a comparison between removal efficiency of amine functionalized carbon nanotube (1), nanomaterial 2 and nanomaterial 3 (initial concentration of methylene blue=100 ppm, dosage of adsorbing material=0.015 mg, temperature=298 K).

Referring now to FIG. 4, it is evident that nanomaterial 3 exhibited better removal efficiency compared with nanomaterial 2 and functionalized carbon nanotube (1). Removal efficiency of nanomaterial 3 is approximately equal to 100% at pH of 5, while removal efficiency of nanomaterial 2 and functionalized carbon nanotube (1) are approximately equal to 77% and 87%, respectively. The removal efficiency increases with increasing pH from 3.0 to 5.0 and then remains constant from 5.0 to 7.0.

The $pK_a$ value of methylene blue was measured to be 3.8 indicating that it can exist in the molecular form below pH 3.8 and has a positive charge beyond this value [Kim, J. R. et al., Am. J. Anal. Chem. 4, 34470, 2013]. At pH lower than 3.8, methylene blue molecules were mainly neutral and did not contribute to ionic/electrostatic interaction with nanomaterial 3. Since methylene blue molecule possesses two aromatic rings with π electrons, nanomaterial 3 adsorbed methylene blue mostly via hydrophobic interaction, π-π stacking, and hydrogen bonding [Qi, C. et al. J. Colloid Interface Sci. 517, 18-27, 2018; He, J. et al. J. Colloid Interface Sci. 512, 190-197, 2018]. At higher pH, methylene blue adsorption significantly improves as reported by others [Gan, D. et al. J. Mol. Liq. 271, 246-253, 2018; Alayan, H. M. et al. Environ. Technol. 40, 2400-2415, 2019]. This can be described by the electrostatic attraction between the positively charged methylene blue (pH>$pK_a$) and the negatively charged surface of nanomaterial 3 basal plane (pH>$pK_a$). Increasing the pH of the solution increases the concentration of hydroxyl groups, therefore, increases the concentration of negatively charged sites and improves the attraction between methylene blue and adsorbent surface [Lai, C. H. et al. Chemosphere 44, 1177-1184, 2001]. However, the constant removal efficiency in this study over the pH range 5 to 7 was an indication that the adsorption of methylene blue on nanomaterial 3 was governed by both the electrostatic interaction and non-electrostatic, e.g. hydrophobic interactions, hydrogen bonds and van der Waals force. It meant that the adsorption of dye from aqueous solution is a complex relationship between non-electrostatic and electrostatic interactions [Moreno-Castilla, C. Carbon 42, 83-94, 2004].

Example 3: Influence of the Nanomaterial Dosage on Removal Efficiency

Dosage of nanomaterial 3 was varied from 0.001 g to 0.08 g under constant experimental conditions to study the removal efficiency of nanomaterials 3 for removal of methylene blue from aqueous solution.

Figure 5:
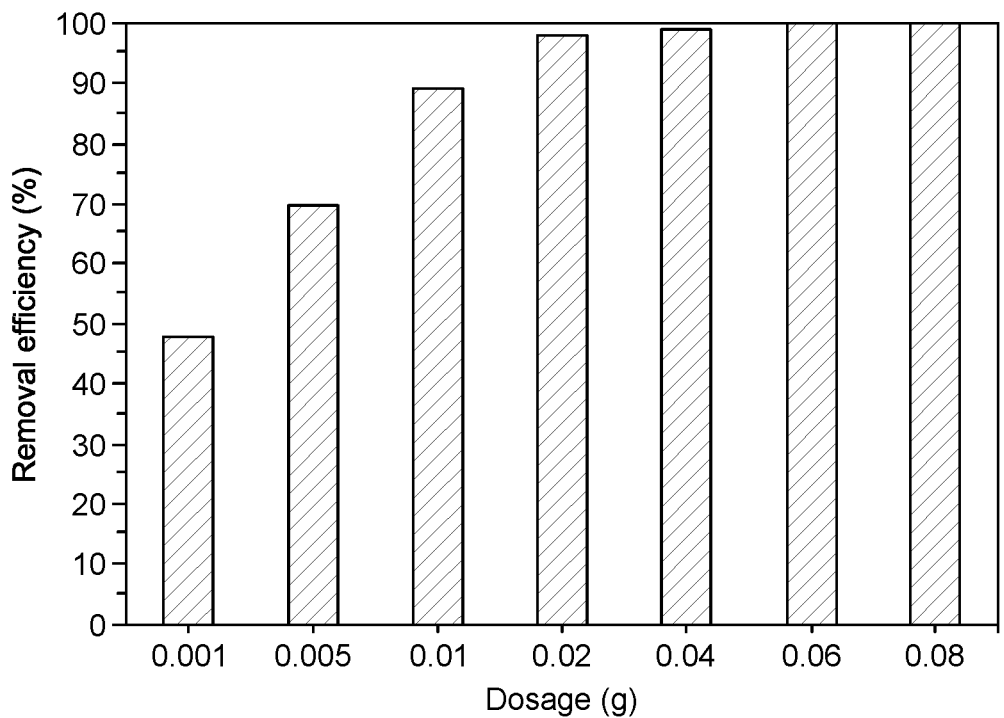
FIG. 5 is a graphical representation showing influence of dosage of nanomaterial 3 on removal efficiency (initial concentration of methylene blue=100 ppm).

Referring now to FIG. 5, it is evident that removal efficiency of nanomaterial 3 increases with increasing dosage. A substantial increase in removal efficiency from 48 to 100% was observed as the dosage of nanomaterial 3 was raised from 0.001 to 0.06 g. This might be ascribed to the availability of an abundant number of adsorption sites at higher concentrations of adsorbents. Nevertheless, no influence of nanomaterial 3 dosage was observed on removal efficiency when the dosage increased from 0.06 to 0.08 g. This indicates that the adsorption reaches an equilibrium between methylene blue molecules adsorbed over nanomaterial 3 and non-adsorbed methylene blue molecules in solution [Saleh, T. A. J. Water Supply Res. Technol. 64, 892-903, 2015].

Example 4: Adsorption Efficiency of Nanomaterial 3 for Industrial Waters

The adsorption efficiency of nanomaterial 3 was evaluated using a real wastewater sample spiked with methylene dye and heavy metal ions. Nanomaterial 3 was added to the wastewater sample and the water was analyzed for concentration of metal ions using inductively coupled plasma.

Referring now to Table 1, pollutants concentrations were significantly decreased which indicates excellent performance of nanomaterial 3 for simultaneous removal of metal ions. The efficacy of nanomaterial 3 could be described by the existence of numerous active sites and motifs on the surface which allows to remove toxic ions such as Ni, Cd, Pb, As, Cr, Cu, Fe in addition to methylene blue.

TABLE 1

Concentrations of pollutants in industrial wastewater before and after treatment with nanomaterial 3 at 298K.

| | Concentration ppb (µg/L) | | |
| --- | --- | --- | --- |
| Pollutant | Initial | After treatment | After spiking followed by treatment |
| Methylene blue | 6 | —* | —* |
| Ni | 194 | 4 | 1 |
| Cd | 19 | —* | 3 |
| Pb | 114 | 2 | 1 |
| As | 29 | —* | 2 |
| Cr | 144 | 7 | 9 |
| Cu | 180 | 25 | 12 |
| Fe | 280 | 20 | 18 |

*below detection limit

Example 5: Adsorption Isotherm for Adsorption of Methylene Blue Over Nanomaterial 3

To understand adsorption behaviors, it is vital to know how methylene blue molecules are distributed between liquid phase and the solid phase at equilibrium. An adsorption isotherm offers valuable information about the binding mechanism, adsorption capacity ($q_t$), as well as the surface properties of the adsorbent. Therefore, Langmuir, Freundlich, and Tempkin isotherm models were applied to evaluate the sorption characteristics of methylene blue over nanomaterial 3.

The adsorption capacity was calculated by equation (2):

$$\text{Adsorption capacity } (q_t) = (c_i - c_t) \times \frac{v}{m} \quad (2)$$

where, $C_i$ and $C_t$ stand for methylene blue initial as well as concentration at time t, v represents volume of methylene blue solution, while m denotes mass of adsorbent.

Figure 6:
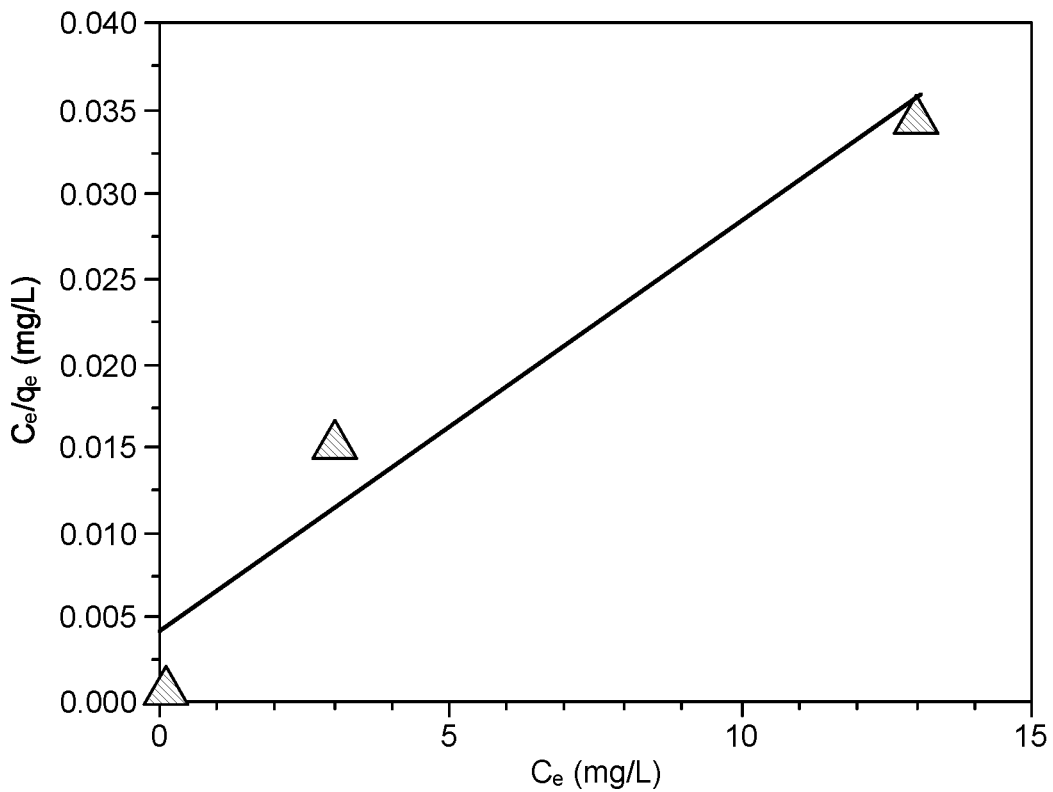
FIG. 6 is a graphical representation showing Langmuir isotherm for methylene blue adsorption over nanomaterial 3 (dosage of nanomaterial 3=0.01 mg, temperature=298 K, pH=6).

Linear form of the Langmuir isotherm model is given by equation (3) [Langmuir, I. J. Am. Chem. Soc. 40, 1361-1403, 1918]:

$$\frac{c_e}{q_e} = \frac{1}{K_L \cdot q_m} + \frac{c_e}{q_m} \quad (3)$$

where, $q_m$ (mg/g) signifies the maximum monolayer adsorption capacity, $K_L$ (L/mg) is Langmuir constant which signifies the binding affinity between the adsorbate and adsorbent, $q_e$ (mg/g) is capacity of adsorption and $C_e$ (mg/L) is adsorbate concentration at equilibrium. Both values of $K_L$ and $q_m$ are obtained from the slope and intercept by plotting $C_e/q_e$ versus $C_e$. The separation factor ($R_L$) in Langmuir model is given by equation (4) [Weber, T. W. et al. AIChE J. 20, 228-238, 1974]:

$$R_L = \frac{1}{(1 + K_L \cdot C_0)} \quad (4)$$

where $C_0$ (mg/L) indicates initial concentration of methylene blue. The $R_L$ value interprets adsorption possibility as: values between 0 and 1 signify favorable adsorption process, value of 1 indicates linear adsorption process, a value greater than 1 means unfavorable adsorption process, while value equal to 0 shows irreversible adsorption. FIG. 6 is a plot of $C_e$ vs $C_e/q_e$ to study the Langmuir isotherm for methylene blue adsorption over nanomaterial 3, with a dosage of 0.01 mg of nanomaterial 3 at a temperature of 298 K and a pH of 6.

Figure 7:
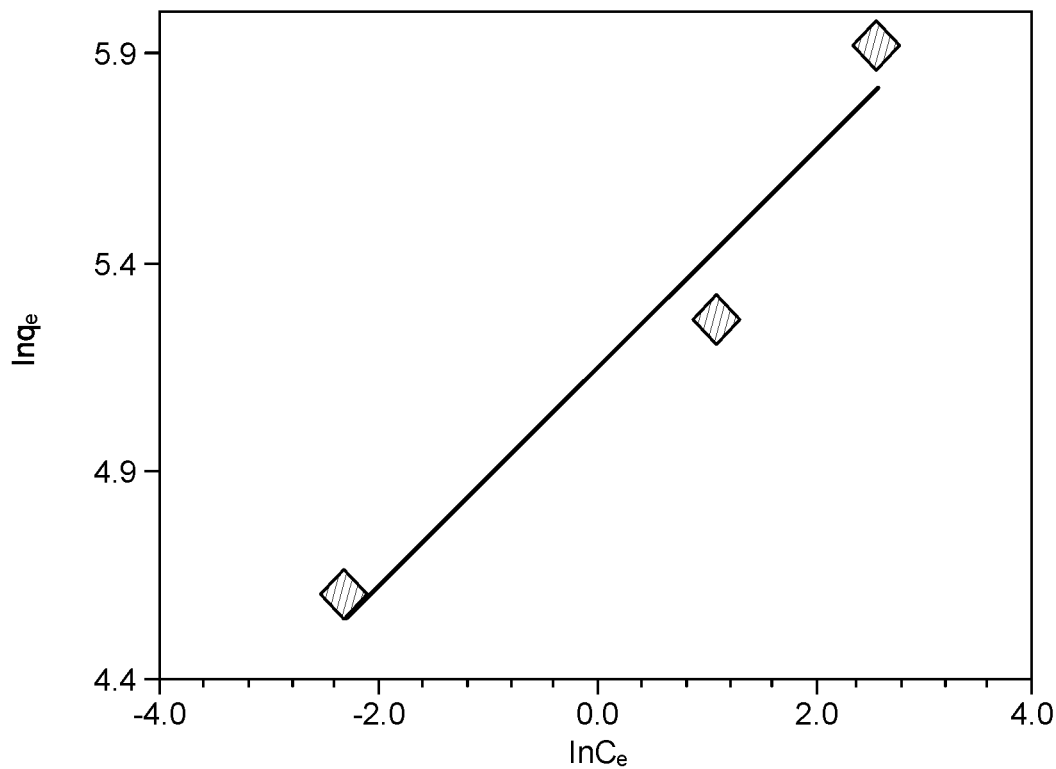
FIG. 7 is a graphical representation showing Freundlich isotherm for methylene blue adsorption over nanomaterial 3 (dosage of nanomaterial 3=0.01 mg, temperature=298 K, pH=6).

The linear form of Freundlich isotherm model is represented in equation (5) [Freundlich, H. M. F. J. Phys. Chem. 57, 1100-1107, 1906]:

$$\ln q_e = \ln K_F + \frac{1}{n} \ln C_e \quad (5)$$

where $K_F$ (mg/g) signifies Freundlich constant which shows adsorption capacities. The 1/n describes intensity of adsorption. The 1/n value indicates the adsorption as favorable (0.1<1/n<0.5) and unfavorable (1/n>2) [Ayub, A. Int. J. Biol. Macromol. 163, 603-617, 2020]. FIG. 7, a plot of ln $C_e$ vs ln $q_e$ to study the Freundlich isotherm for methylene blue adsorption over nanomaterial 3, with a dosage of 0.01 mg of nanomaterial 3 at a temperature of 298 K and a pH of 6.

Figure 8:
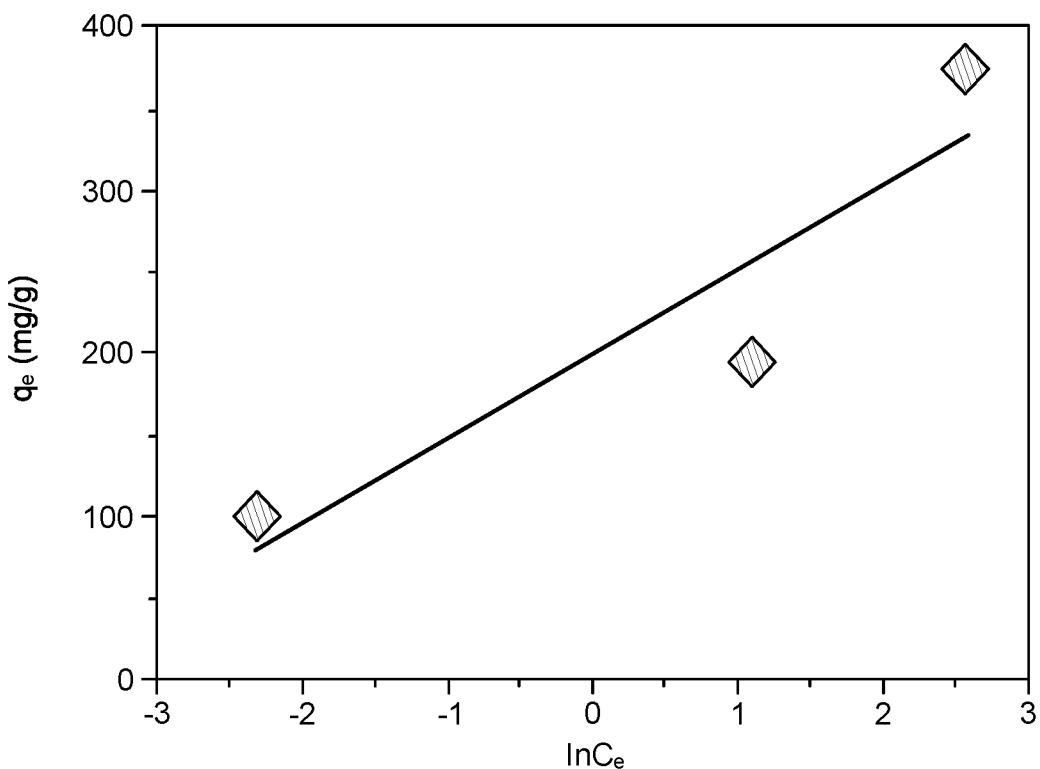
FIG. 8 is a graphical representation showing Temkin isotherm for methylene blue adsorption over nanomaterial 3 (dosage of nanomaterial 3=0.01 mg, temperature=298 K, pH=6).

The linear equation of Temkin isotherm expression is given by equation (6) [Tempkin, M. I. et al. Acta Phys. Chim. 12, 327, 1940]:

$$q_e = \frac{RT}{b_T} \ln K_T + \frac{RT}{b_T} \ln C_e \quad (6)$$

where, $K_T$ (L/g) is Temkin isotherm constant, $b_T$ (J/mol) is the equilibrium binding constant while T and R represent temperature and gas constant. FIG. 8 is a plot of ln $C_e$ vs $q_e$ to study the Temkin isotherm for methylene blue adsorption over nanomaterial 3, with a dosage of 0.01 mg of nanomaterial 3 at a temperature of 298 K and a pH of 6.

Referring now to Table 2, Langmuir and Freundlich model showed a good fit to experimental adsorption data for adsorption of methylene blue over nanomaterial 3. Maximum monolayer adsorption capacity ($q_m$) of nanomaterial 3 for methylene blue was found to be 416.7 mg/g. The separation factor ($R_L$) was found to be 0.819 indicating a favorable adsorption process. However, Freundlich isotherm displayed better fit to the experimental data with a correlation coefficients ($R_2$) of 0.975. Furthermore, these results also imply a heterogeneous distribution of active sites on nanomaterial 3 surface. The value of n was higher than unity at equilibrium, suggesting a favorable adsorption [Wu, Z. et al. RSC Adv. 10, 10703-10714, 2020].

209-217, 2015]. During initial 5 min, fast methylene blue adsorption behavior was observed at an initial concentration of 50 ppm and more than half the amount of methylene blue molecules were adsorbed. This might be contributed to the formation of π-π stacking interaction between the aromatic rings of the adsorbed methylene blue molecules and aromatic rings of nanomaterial 3 [Bin-Dahman, O. A. et al. Environ. Nanotechnology, Monit. Manag. 13, 100286, 2020]. In addition, the aligned porous structure assisted the interaction between the methylene blue and multi-walled carbon nanotubes [Papa, E. et al. J. Colloid Interface Sci. 572, 364-373, 2020]. The adsorption further increased at a slower rate and finally, equilibrium was attained in 70 min. This rapid-kinetic behavior shows that the sorption relies on the accessible binding sites on the adsorbent for the removal of

TABLE 2

The parameters of isotherm models of MB dye removal by compound 3.

| Langmuir | | | Freundlich | | | | Temkin | | |
|---|---|---|---|---|---|---|---|---|---|
| $q_m$ (mg/g) | $K_L$ (L/mg) | $R^2$ | 1/n | n | $K_F$ | $R^2$ | $b_T$ (KJ/mol) | $K_T$ (L/g) | $R^2$ |
| 416.7 | 0.002 | 0.951 | 0.26 | 3.88 | 181.27 | 0.975 | 9.603 | 1.01 | 0.845 |

Example 6: Kinetics Study for Adsorption of Methylene Blue Over Nanomaterial 3

The mechanisms of adsorption and potential rate-controlling stages of methylene blue adsorption over nanomaterial 3 were analyzed with pseudo-first and -second order kinetic models. Equation (7) represents linearized mathematical equation for the first-order kinetic model [Lagergren, S. K. Sven. Vetenskapsakad. Handingarl. 24, 1-39, 1898]:

$$\ln(q_e - q_t) = \ln q_e - k_1 t \quad (7)$$

where $q_e$ and $q_t$ denotes adsorption capacities of methylene blue in mg/g at equilibrium and at time t (min), respectively, while $k_1$ (min-1) signifies a first-order rate constant.

Figure 9:
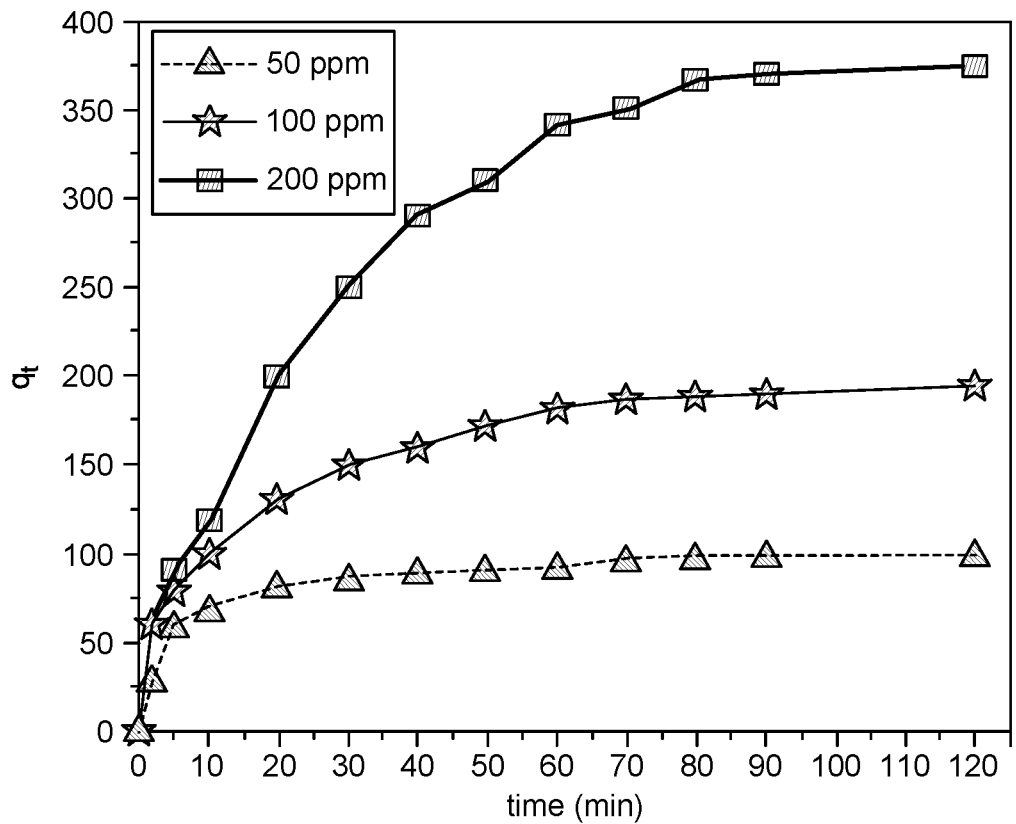
FIG. 9 is a graphical representation showing variation in adsorption capacity ($q_t$) of nanomaterial 3 with adsorption contact time at different initial concentrations of methylene blue.

Equation (8) represents a second order kinetic model [Weber Jr, W. J. et al. J. Sanit. Eng. Div. 89, 31-59, 1963]:

$$\frac{t}{q_t} = \frac{1}{k_2 \cdot q_e^2} + \frac{t}{q_e} \quad (8)$$

where, $q_t$ and $q_e$ show the quantity of methylene blue sorbed (mg/g) by adsorbent at time t (min) and at equilibrium, while $k_2$ (g/mg·min) indicates a second-order rate constant. FIG. 9 shows variation in the adsorption capacity ($q_t$) with contact time for methylene blue over nanomaterial 3 at different initial concentrations ranging from 50 to 200 parts per million (ppm). MWCNs can adsorb the methylene blue by hydrogen bond, electrostatic and π-π stacking interactions [Ghaffar, A. et al. Green Process. Synth. 4, methylene blue. In 70 min, the surfaces of nanomaterial 3 becomes completely saturated with the methylene blue species and finally, dynamic equilibrium was attained. There are repulsive forces existed by dye molecule which caused the sites of adsorbent to be difficult to occupy at equilibrium [Ding, F. et al. Int. J. Biol. Macromol. 182, 750-759, 2021].

Figure 10:
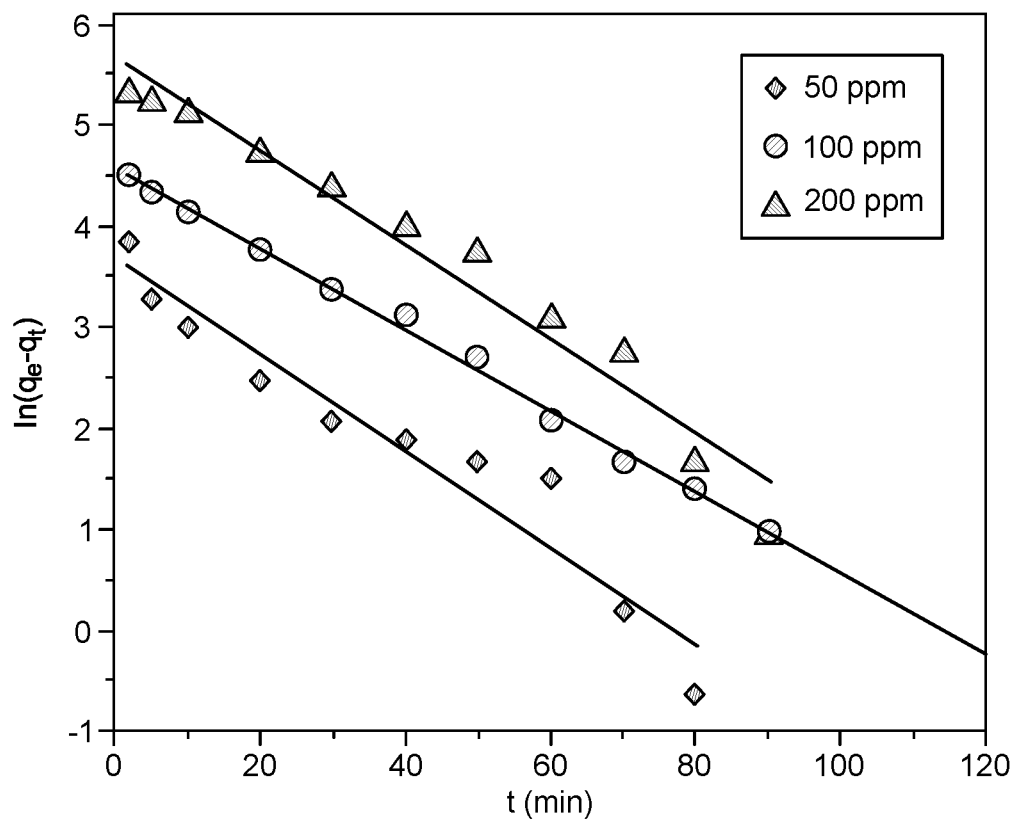
FIG. 10 is a graphical representation showing pseudo-first order model for variation in adsorption capacity ($q_t$) of nanomaterial 3 with adsorption contact time at different initial concentrations of methylene blue.
Figure 11:
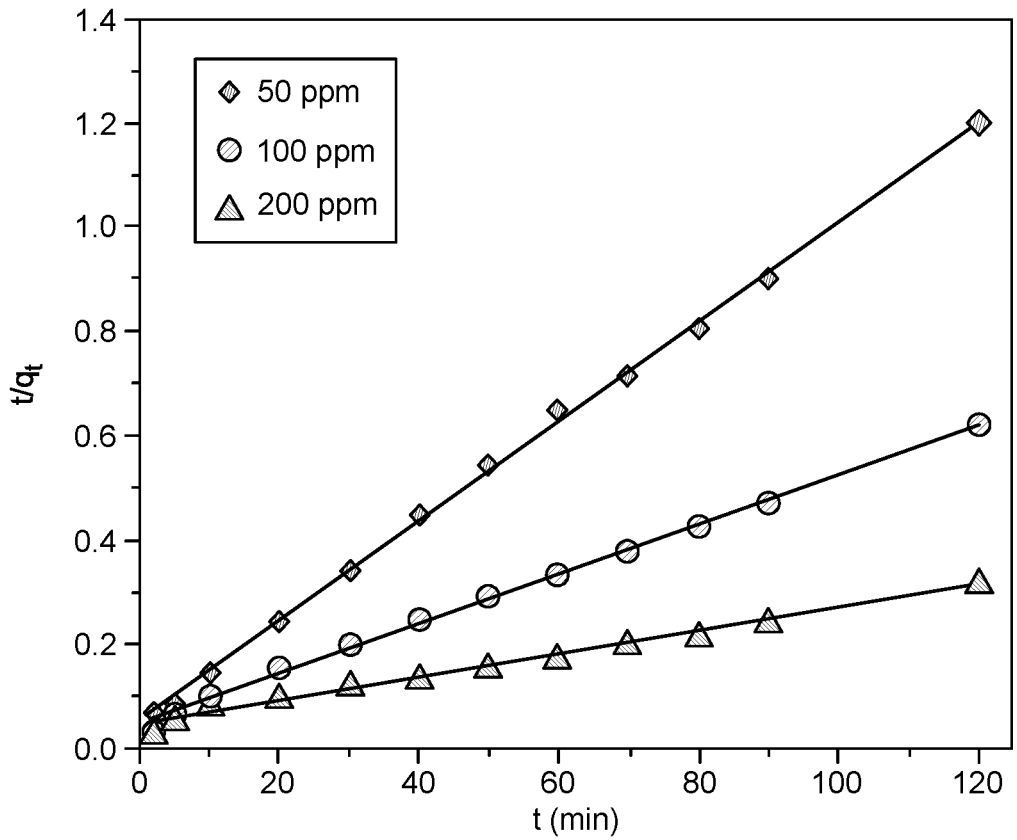
FIG. 11 is a graphical representation showing pseudo-second order model for variation in adsorption capacity ($q_t$) of nanomaterial 3 with adsorption contact time at different initial concentrations of methylene blue.

The amount of methylene blue adsorbed per unit mass of nanomaterial 3 at equilibrium, i.e. the equilibrium adsorption capacity ($q_e$), increased with increasing methylene blue initial concentrations. To understand the adsorption process, the experimental data was examined by pseudo-first and pseudo-second order kinetic models. FIGS. 10 & 11 shows a pseudo-first order model and a pseudo-second order model, respectively for variation in adsorption capacity ($q_t$) with contact time for adsorption of methylene blue onto nanomaterial 3 at different initial concentrations ranging from 50 to 200 ppm.

Referring now to Table 3, pseudo-second order kinetic model was detected to fit better and explain the kinetics of methylene blue adsorption over nanomaterial 3 because it displayed high values of linear regression coefficient ($R_2$) when compared with pseudo first-order model. The rational agreement between the computed $q_e$ ($q_e$ comp) and experimental $q_e$ ($q_e$ exp) supports the validity of the pseudo-second order kinetic model. These results suggest that the adsorption of methylene blue on nanomaterial 3 takes place via chemisorption mechanisms [Hosseini, S. et al. Chem. Eng. J. 171, 1124-1131, 2011]. The results agree with previous work [Ding, F. et al. Int. J. Biol. Macromol. 182, 750-759, 2021] using hollow cellulose-carbon nanotubes composite.

TABLE 3

Parameters of Kinetic model for MB removal on compound 3 at 298 K

| | | Pseudo first order | | | Pseudo second order | | |
|---|---|---|---|---|---|---|---|
| $C_i$ (mg/L) | $q_e$ exp (mg/g) | $k_1$ (min$^{-1}$) | $q_e$ comp (mg/g) | $R^2$ | $k_2$ (g/mg · min) | $q_e$ comp (mg/g) | $R^2$ |
| 50 | 99.8 | 0.047 | 58.475 | 0.933 | 0.0018 | 104.17 | 0.999 |
| 100 | 194.0 | 0.04 | 145.474 | 0.9963 | 0.0005 | 208.33 | 0.997 |
| 200 | 374.0 | 0.0466 | 445.858 | 0.961 | 0.0001 | 454.55 | 0.989 |

Obviously, numerous modifications and variations of the present disclosure are possible in light of the above teachings. It is therefore to be understood that within the scope of the appended claims, the invention may be practiced otherwise than as specifically described herein.

What is claimed is:

1. A solid nanomaterial adsorbent, which is a product, in the form of a powder, formed by a reaction of:
   a functionalized carbon nanotube comprising first and second aminoalkyl groups covalently bonded to a surface of the carbon nanotube; and
   a porphyrin ring of formula (I)

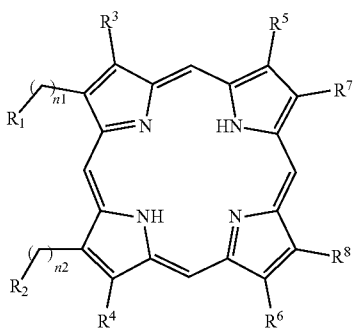

(I)

or a salt thereof, a solvate thereof, a tautomer thereof, a stereoisomer thereof, a metalation product thereof, or a mixture thereof,
wherein:
the first and second aminoalkyl groups are each independently a $C_{1-6}$ alkyl substituted with at least one primary or secondary amino group;
$R_1$ and $R_2$ are —COOH;
$R_3$ and $R_4$ are —CH$_3$;
$R_5$, $R_6$, $R_7$, and $R_8$ are each independently selected from the group consisting of a hydrogen, an optionally substituted $C_{1-6}$ alkyl, an optionally substituted $C_{1-6}$ cycloalkyl, and an optionally substituted $C_{1-6}$ alkenyl;
$n_1$ and $n_2$ are 1; and
the functionalized carbon nanotube is bonded with the porphyrin ring of formula (I) via two amide linkages, one formed between $R_1$ of the porphyrin ring and the first aminoalkyl group of the functionalized carbon nanotube, and the other between $R_2$ of the porphyrin ring and the second aminoalkyl group of the functionalized carbon nanotube.

2. The solid nanomaterial adsorbent of claim 1, wherein the functionalized carbon nanotube is a multi-walled carbon nanotube.

3. The solid nanomaterial adsorbent of claim 1, wherein the first and second aminoalkyl groups are —CH$_2$CH$_2$NH$_2$.

4. The solid nanomaterial adsorbent of claim 1, wherein $R_5$ and $R_8$ are independently —CH$_3$ or —CH=CH$_2$.

5. The solid nanomaterial adsorbent of claim 1, wherein $R_6$ and $R_7$ are independently —CH$_3$ or —CH(OH)CH$_3$.

6. The solid nanomaterial adsorbent of claim 1, wherein the porphyrin ring is

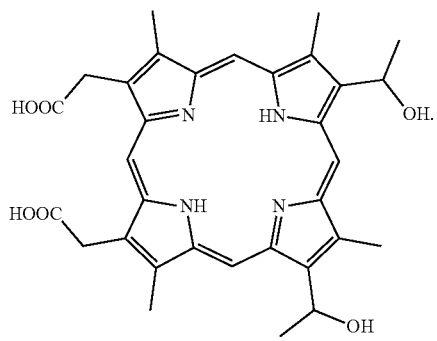 [SMILES: CC1=C(CC(=O)O)c2cc3[nH]c(cc4nc(cc5[nH]c(cc1n2)c(C)c5C(C)O)C(C)=C4C(C)O)c(C)c3CC(=O)O]

7. The solid nanomaterial adsorbent of claim 1, wherein the porphyrin ring is a metalation product of formula (I), and the porphyrin ring is of formula (II)

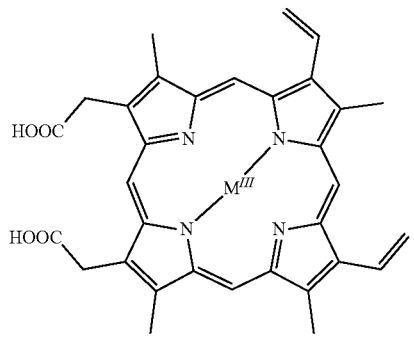

(II)

wherein M is a metal selected from the group consisting of Mn, Fe, and Co.

8. The solid nanomaterial adsorbent of claim 1, wherein a shortest distance between the first and second aminoalkyl groups on the surface of the functionalized carbon nanotube is about 0.1-10 nm.

9. A method of preparing the solid nanomaterial adsorbent of claim 1, the method comprising:
   mixing the functionalized carbon nanotube with the porphyrin ring of formula (I) thereby forming the solid nanomaterial adsorbent.

10. The method of claim 9, wherein the mixing occurs in the presence of an amide bond formation coupling reagent.

11. The method of claim 9, wherein the first and second aminoalkyl groups are —$CH_2CH_2NH_2$, and the amine functionalized carbon nanotube is prepared by mixing a carbon nanotube with ethylene diamine in the presence of a nitrite salt and a strong acid.

12. A method for removing a pollutant from an aqueous solution, the method comprising:
    contacting the aqueous solution having an initial concentration of the pollutant with the solid nanomaterial adsorbent of claim 1 to form a mixture; and
    filtering the mixture to obtain an aqueous solution having a reduced concentration of the pollutant compared to the initial concentration,
    wherein:
    the initial concentration of the pollutant in the aqueous solution is in a range of 10 to 1,000 mg $L^{-1}$;
    the solid nanomaterial adsorbent is present in a concentration ranging from 0.001 to 10 g per liter of the aqueous solution during the contacting; and
    the solid nanomaterial adsorbent is contacted with the aqueous solution at a temperature in a range of 10° ° C. to 80° C. for 0.1 to 24 hours.

13. The method of claim 12, wherein the pollutant is an organic dye, a heavy metal, or both.

14. The method of claim 13, wherein the pollutant is an organic dye, and wherein the organic dye is methylene blue.

15. The method of claim 13, wherein the pollutant is a heavy metal, and wherein the heavy metal is an ion of at least one heavy metal selected from the group consisting of Ni, Cd, Pb, As, Cr, Cu, and Fe.

16. The method of claim 12, wherein the aqueous solution has a pH in a range of 3 to 7.

17. The method of claim 12, wherein greater than 75% of a total mass of the pollutant is removed from the aqueous solution.

* * * * *